United States Patent
Sengun

(10) Patent No.: US 12,369,902 B2
(45) Date of Patent: Jul. 29, 2025

(54) SYSTEMS, DEVICES, AND METHODS FOR SECURING TISSUE USING HARD ANCHORS

(71) Applicant: Medos International Sàrl, Le Locle (CH)

(72) Inventor: Mehmet Ziya Sengun, Canton, MA (US)

(73) Assignee: Medos International Sàrl, Le Locle (CH)

( * ) Notice: Subject to any disclaimer, the term of this patent is extended or adjusted under 35 U.S.C. 154(b) by 0 days.

(21) Appl. No.: 18/183,785

(22) Filed: Mar. 14, 2023

(65) Prior Publication Data

US 2023/0210517 A1    Jul. 6, 2023

Related U.S. Application Data

(63) Continuation of application No. 16/887,683, filed on May 29, 2020, now Pat. No. 11,672,523, which is a (Continued)

(51) Int. Cl.
*A61B 17/04* (2006.01)
*A61B 17/00* (2006.01)
(Continued)

(52) U.S. Cl.
CPC .... *A61B 17/0401* (2013.01); *A61B 17/06166* (2013.01); *A61F 2/0811* (2013.01);
(Continued)

(58) Field of Classification Search
CPC ............... A61B 17/04; A61B 17/0401; A61B 17/0469; A61B 17/06166; A61B 17/0642;
(Continued)

(56) References Cited

U.S. PATENT DOCUMENTS 2,566,625 A  9/1951 Nagelmann
2,600,395 A  6/1952 Joseph et al.
(Continued)

FOREIGN PATENT DOCUMENTS

AU    724861 B2    10/2000
AU    2008229746 B2    3/2011
(Continued)

OTHER PUBLICATIONS

Adjacent Definition & Meaning Merriam-Webster, https://www.merriam-webster.com/dictionary/adjacent, accessed Nov. 21, 24 (Year: 2024).*
(Continued)

*Primary Examiner* — Kankindi Rwego
(74) *Attorney, Agent, or Firm* — Barnes & Thornburg LLP

(57) ABSTRACT

Systems, devices, and methods are provided for securing soft tissue to bone. One exemplary embodiment of a device includes an anchor, a repair filament, and a connecting filament that is coupled to the repair filament, is in contact with the anchor's distal end, and is effective to connect the repair filament to the anchor such that the repair filament slides with respect to the anchor. The anchor can be rigid, and can include an axial bore extending therethrough. At least one of the repair filament and the connecting filament can extend through at least a portion of the axial bore, and the bore can be sized such that a portion of the filament extending therethrough barely fits to help maintain the connection between the anchor, repair filament, and connecting filament. Embodiments of the systems and devices disclosed can be used in a number of methods for repairing soft tissue.

29 Claims, 14 Drawing Sheets

Related U.S. Application Data continuation of application No. 15/692,885, filed on Aug. 31, 2017, now Pat. No. 10,695,047, which is a continuation of application No. 13/623,429, filed on Sep. 20, 2012, now Pat. No. 9,763,655.

(51) Int. Cl.
*A61B 17/06* (2006.01)
*A61F 2/08* (2006.01)

(52) U.S. Cl.
CPC .............. *A61B 2017/00336* (2013.01); *A61B 2017/00845* (2013.01); *A61B 2017/00849* (2013.01); *A61B 2017/0409* (2013.01); *A61B 2017/0414* (2013.01); *A61B 2017/0458* (2013.01); *A61B 2017/0475* (2013.01); *A61B 2017/06185* (2013.01); *A61F 2002/0841* (2013.01); *A61F 2002/0888* (2013.01)

(58) Field of Classification Search
CPC ........... A61B 2017/00336; A61B 2017/00845; A61B 2017/00849; A61B 2017/0403; A61B 2017/0408; A61B 2017/0409; A61B 2017/0412; A61B 2017/0414; A61B 2017/0448; A61B 2017/0451; A61B 2017/0454; A61B 2017/0458; A61B 2017/0462; A61B 2017/0475; A61B 2017/0477; A61B 2017/06185; A61F 2/0811; A61F 2002/0841; A61F 2002/0888
USPC ........................................................ 606/232
See application file for complete search history.

(56) References Cited

U.S. PATENT DOCUMENTS

| | | |
|---|---|---|
| 2,697,624 A | 12/1954 | Thomas et al. |
| 2,758,858 A | 8/1956 | Smith, Sr. |
| 2,992,029 A | 7/1961 | Russell |
| 3,106,417 A | 10/1963 | Clow |
| 3,131,957 A | 5/1964 | Musto |
| 3,177,021 A | 4/1965 | Benham |
| 3,402,957 A | 9/1968 | Peterson |
| 3,521,918 A | 7/1970 | Hammond |
| 3,565,077 A | 2/1971 | Glick |
| 3,580,256 A | 5/1971 | Wilkinson et al. |
| 3,712,651 A | 1/1973 | Shockley |
| 3,752,516 A | 8/1973 | Mumma |
| 3,873,140 A | 3/1975 | Bloch |
| 4,029,346 A | 6/1977 | Browning |
| 4,036,101 A | 7/1977 | Burnett |
| 4,038,988 A | 8/1977 | Perisse |
| 4,105,034 A | 8/1978 | Shalaby et al. |
| 4,130,639 A | 12/1978 | Shalaby et al. |
| 4,140,678 A | 2/1979 | Shalaby et al. |
| 4,141,087 A | 2/1979 | Shalaby et al. |
| 4,186,921 A | 2/1980 | Fox |
| 4,205,399 A | 6/1980 | Shalaby et al. |
| 4,208,511 A | 6/1980 | Shalaby et al. |
| 4,319,428 A | 3/1982 | Fox |
| 4,403,797 A | 9/1983 | Ragland, Jr. |
| 4,510,934 A | 4/1985 | Batra |
| 4,572,554 A | 2/1986 | Janssen et al. |
| 4,792,336 A | 12/1988 | Hlavacek et al. |
| 4,870,957 A | 10/1989 | Goble et al. |
| 4,946,377 A | 8/1990 | Kovach |
| 4,962,929 A | 10/1990 | Melton, Jr. |
| 4,987,665 A | 1/1991 | Dumican et al. |
| 5,062,344 A | 11/1991 | Gerker |
| 5,098,137 A | 3/1992 | Wardall |
| 5,144,961 A | 9/1992 | Chen et al. |
| 5,156,616 A | 10/1992 | Meadows et al. |
| 5,178,629 A | 1/1993 | Kammerer |
| 5,217,495 A | 6/1993 | Kaplan et al. |
| 5,250,053 A | 10/1993 | Snyder |
| 5,250,054 A | 10/1993 | Li |
| 5,259,846 A | 11/1993 | Granger et al. |
| 5,263,984 A | 11/1993 | Li et al. |
| 5,279,311 A | 1/1994 | Snyder |
| 5,282,809 A | 2/1994 | Kammerer et al. |
| 5,284,485 A | 2/1994 | Kammerer et al. |
| 5,312,423 A | 5/1994 | Rosenbluth et al. |
| 5,318,575 A | 6/1994 | Chesterfield et al. |
| 5,320,629 A | 6/1994 | Noda et al. |
| 5,374,278 A | 12/1994 | Chesterfield et al. |
| 5,376,118 A | 12/1994 | Kaplan et al. |
| 5,391,176 A | 2/1995 | de la Torre |
| 5,395,382 A | 3/1995 | DiGiovanni et al. |
| 5,405,352 A | 4/1995 | Weston |
| 5,450,860 A | 9/1995 | O'Connor |
| 5,454,820 A | 10/1995 | Kammerer et al. |
| 5,456,722 A | 10/1995 | McLeod et al. |
| 5,464,427 A | 11/1995 | Curtis et al. |
| 5,464,929 A | 11/1995 | Bezwada et al. |
| 5,472,446 A | 12/1995 | de la Torre |
| 5,527,323 A | 6/1996 | Jervis et al. |
| 5,534,011 A | 7/1996 | Greene, Jr. et al. |
| 5,540,703 A | 7/1996 | Barker, Jr. et al. |
| 5,549,618 A | 8/1996 | Fleenor et al. |
| 5,562,684 A * | 10/1996 | Kammerer ......... A61B 17/0401 606/139 |
| 5,569,306 A | 10/1996 | Thal |
| 5,571,139 A | 11/1996 | Jenkins, Jr. |
| 5,573,286 A | 11/1996 | Rogozinski |
| 5,591,207 A | 1/1997 | Coleman |
| 5,593,189 A | 1/1997 | Little |
| 5,595,751 A | 1/1997 | Bezwada et al. |
| 5,597,579 A | 1/1997 | Bezwada et al. |
| 5,607,687 A | 3/1997 | Bezwada et al. |
| 5,618,552 A | 4/1997 | Bezwada et al. |
| 5,620,698 A | 4/1997 | Bezwada et al. |
| 5,628,756 A | 5/1997 | Barker, Jr. et al. |
| 5,645,850 A | 7/1997 | Bezwada et al. |
| 5,647,616 A | 7/1997 | Hamilton |
| 5,647,874 A | 7/1997 | Hayhurst |
| 5,648,088 A | 7/1997 | Bezwada et al. |
| 5,667,528 A | 9/1997 | Colligan |
| 5,683,417 A | 11/1997 | Cooper |
| 5,683,419 A | 11/1997 | Thal |
| 5,685,037 A | 11/1997 | Fitzner et al. |
| 5,697,950 A | 12/1997 | Fucci et al. |
| 5,698,213 A | 12/1997 | Jamiolkowski et al. |
| 5,700,583 A | 12/1997 | Jamiolkowski et al. |
| 5,702,397 A | 12/1997 | Goble et al. |
| 5,709,708 A | 1/1998 | Thal |
| 5,716,368 A | 2/1998 | de la Torre et al. |
| 5,725,556 A | 3/1998 | Moser et al. |
| 5,728,109 A | 3/1998 | Schulze et al. |
| 5,741,332 A | 4/1998 | Schmitt |
| 5,749,898 A | 5/1998 | Schulze et al. |
| 5,782,864 A | 7/1998 | Lizardi |
| 5,814,069 A | 9/1998 | Schulze et al. |
| 5,859,150 A | 1/1999 | Jamiolkowski et al. |
| 5,899,920 A | 5/1999 | DeSatnick et al. |
| 5,941,900 A | 8/1999 | Bonutti |
| 5,964,783 A | 10/1999 | Grafton et al. |
| 5,971,447 A | 10/1999 | Steck, III |
| 5,989,252 A | 11/1999 | Fumex |
| 6,024,758 A | 2/2000 | Thal |
| 6,045,574 A | 4/2000 | Thal |
| 6,143,017 A | 11/2000 | Thal |
| 6,221,084 B1 | 4/2001 | Fleenor |
| 6,267,766 B1 | 7/2001 | Burkhart |
| 6,296,659 B1 | 10/2001 | Foerster |
| 6,299,612 B1 | 10/2001 | Ouchi |
| 6,319,271 B1 | 11/2001 | Schwartz et al. |
| 6,322,112 B1 | 11/2001 | Duncan |
| 6,517,578 B2 | 2/2003 | Hein |
| 6,527,794 B1 | 3/2003 | McDevitt et al. |
| 6,527,795 B1 | 3/2003 | Lizardi |
| 6,540,750 B2 | 4/2003 | Burkhart |
| 6,547,807 B2 | 4/2003 | Chan et al. |

(56) References Cited

U.S. PATENT DOCUMENTS

| | | |
|---|---|---|
| 6,596,015 B1 | 7/2003 | Pitt et al. |
| 6,641,596 B1 | 11/2003 | Lizardi |
| 6,641,597 B2 | 11/2003 | Burkhart et al. |
| 6,652,563 B2 | 11/2003 | Dreyfuss |
| 6,660,023 B2 | 12/2003 | McDevitt et al. |
| 6,689,154 B2 | 2/2004 | Bartlett |
| 6,716,234 B2 | 4/2004 | Grafton et al. |
| 6,767,037 B2 | 7/2004 | Wenstrom, Jr. |
| 6,818,010 B2 | 11/2004 | Eichhorn et al. |
| 6,887,259 B2 | 5/2005 | Lizardi |
| 6,923,824 B2 | 8/2005 | Morgan et al. |
| 6,994,719 B2 | 2/2006 | Grafton |
| 7,029,490 B2 | 4/2006 | Grafton et al. |
| 7,048,754 B2 | 5/2006 | Martin et al. |
| 7,081,126 B2 | 7/2006 | McDevitt et al. |
| 7,217,279 B2 | 5/2007 | Reese |
| 7,226,469 B2 | 6/2007 | Benavitz et al. |
| 7,235,090 B2 | 6/2007 | Buckman et al. |
| 7,285,124 B2 | 10/2007 | Foerster |
| 7,309,337 B2 | 12/2007 | Colleran et al. |
| 7,338,502 B2 | 3/2008 | Rosenblatt |
| 7,381,213 B2 | 6/2008 | Lizardi |
| 7,390,332 B2 | 6/2008 | Selvitelli et al. |
| 7,455,684 B2 | 11/2008 | Gradel et al. |
| 7,582,105 B2 | 9/2009 | Kolster |
| 7,601,165 B2 | 10/2009 | Stone |
| 7,651,509 B2 | 1/2010 | Bojarski et al. |
| 7,654,321 B2 | 2/2010 | Zazovsky et al. |
| 7,658,750 B2 | 2/2010 | Li |
| 7,658,751 B2 | 2/2010 | Stone et al. |
| 7,682,374 B2 | 3/2010 | Foerster et al. |
| 7,695,495 B2 | 4/2010 | Dreyfuss |
| 7,703,372 B1 | 4/2010 | Shakespeare |
| 7,803,173 B2 | 9/2010 | Burkhart et al. |
| 7,875,043 B1 | 1/2011 | Ashby et al. |
| 7,883,528 B2 | 2/2011 | Grafton et al. |
| 7,883,529 B2 | 2/2011 | Sinnott et al. |
| 7,905,903 B2 | 3/2011 | Stone et al. |
| 7,905,904 B2 | 3/2011 | Stone et al. |
| 7,959,650 B2 | 6/2011 | Kaiser et al. |
| 7,981,140 B2 | 7/2011 | Burkhart |
| 8,012,171 B2 | 9/2011 | Schmieding |
| 8,088,130 B2 | 1/2012 | Kaiser et al. |
| 8,088,146 B2 | 1/2012 | Wert et al. |
| 8,114,128 B2 | 2/2012 | Cauldwell et al. |
| 8,118,836 B2 | 2/2012 | Denham et al. |
| 8,128,658 B2 | 3/2012 | Kaiser et al. |
| 8,137,382 B2 | 3/2012 | Denham et al. |
| 8,231,653 B2 | 7/2012 | Dreyfuss |
| 8,231,654 B2 | 7/2012 | Kaiser et al. |
| 8,323,316 B2 | 12/2012 | Maiorino et al. |
| 8,419,769 B2 | 4/2013 | Thal |
| 8,545,535 B2 | 10/2013 | Hirotsuka et al. |
| 8,608,758 B2 | 12/2013 | Singhatat et al. |
| 8,790,369 B2 | 7/2014 | Orphanos et al. |
| 8,790,370 B2 | 7/2014 | Spenciner et al. |
| 8,814,905 B2 | 8/2014 | Sengun et al. |
| 8,821,543 B2 | 9/2014 | Hernandez et al. |
| 8,821,544 B2 | 9/2014 | Sengun et al. |
| 8,821,545 B2 | 9/2014 | Sengun |
| 8,894,684 B2 | 11/2014 | Sengun |
| 8,974,495 B2 | 3/2015 | Hernandez et al. |
| 9,017,381 B2 | 4/2015 | Kaiser et al. |
| 9,034,013 B2 | 5/2015 | Sengun |
| 9,060,763 B2 | 6/2015 | Sengun |
| 9,060,764 B2 | 6/2015 | Sengun |
| 9,095,331 B2 | 8/2015 | Hernandez et al. |
| 9,179,908 B2 | 11/2015 | Sengun |
| 9,192,373 B2 | 11/2015 | Sengun |
| 9,198,653 B2 | 12/2015 | Sengun et al. |
| 9,271,716 B2 | 3/2016 | Sengun |
| 9,345,468 B2 | 5/2016 | Sengun et al. |
| 9,345,567 B2 | 5/2016 | Sengun |
| 9,393,007 B2 | 7/2016 | Darois et al. |
| 9,510,819 B2 | 12/2016 | Stone et al. |
| 9,532,778 B2 | 1/2017 | Sengun et al. |
| 9,737,293 B2 | 8/2017 | Sengun et al. |
| 9,757,116 B2 | 9/2017 | Sengun |
| 9,763,655 B2 | 9/2017 | Sengun |
| 9,795,373 B2 | 10/2017 | Sengun |
| 9,833,229 B2 | 12/2017 | Hernandez et al. |
| 9,872,678 B2 | 1/2018 | Spenciner et al. |
| 9,895,145 B2 | 2/2018 | Sengun et al. |
| 10,258,321 B2 | 4/2019 | Sengun |
| 10,271,833 B2 | 4/2019 | Sengun |
| 10,292,695 B2 | 5/2019 | Sengun et al. |
| 10,524,777 B2 | 1/2020 | Sengun |
| 10,631,848 B2 | 4/2020 | Sengun et al. |
| 10,695,047 B2 | 6/2020 | Sengun |
| 10,736,624 B2 | 8/2020 | Sauer |
| 10,751,041 B2 | 8/2020 | Spenciner et al. |
| 10,835,231 B2 | 11/2020 | Hernandez et al. |
| 10,912,549 B2 | 2/2021 | Sengun et al. |
| 11,039,827 B2 | 6/2021 | Sengun et al. |
| 11,272,915 B2 | 3/2022 | Sengun |
| 11,672,522 B2 | 6/2023 | Sengun et al. |
| 11,672,523 B2 | 6/2023 | Sengun |
| 11,771,414 B2 | 10/2023 | Spenciner et al. |
| 2002/0019649 A1 | 2/2002 | Sikora et al. |
| 2002/0029066 A1 | 3/2002 | Foerster |
| 2003/0004545 A1 | 1/2003 | Burkhart et al. |
| 2003/0023268 A1 | 1/2003 | Lizardi |
| 2003/0050667 A1 | 3/2003 | Grafton et al. |
| 2003/0120309 A1 | 6/2003 | Colleran et al. |
| 2003/0130695 A1 | 7/2003 | McDevitt et al. |
| 2003/0229362 A1 | 12/2003 | Chan et al. |
| 2004/0093031 A1 | 5/2004 | Burkhart et al. |
| 2004/0098050 A1 | 5/2004 | Foerster et al. |
| 2004/0153074 A1 | 8/2004 | Bojarski et al. |
| 2004/0172062 A1 | 9/2004 | Burkhart |
| 2004/0199185 A1 | 10/2004 | Davignon |
| 2004/0236373 A1 | 11/2004 | Anspach, III |
| 2005/0033363 A1 | 2/2005 | Bojarski et al. |
| 2005/0119696 A1 | 6/2005 | Walters et al. |
| 2005/0137624 A1 | 6/2005 | Fallman |
| 2005/0165416 A1 | 7/2005 | Bojarski et al. |
| 2005/0187577 A1 | 8/2005 | Selvitelli et al. |
| 2005/0251208 A1 | 11/2005 | Elmer et al. |
| 2006/0106423 A1 | 5/2006 | Welsel et al. |
| 2006/0178680 A1 | 8/2006 | Nelson et al. |
| 2006/0178702 A1 | 8/2006 | Pierce et al. |
| 2006/0259076 A1 | 11/2006 | Burkhart et al. |
| 2006/0293710 A1 | 12/2006 | Foerster et al. |
| 2007/0027476 A1 | 2/2007 | Harris et al. |
| 2007/0032792 A1 | 2/2007 | Collin et al. |
| 2007/0060922 A1* | 3/2007 | Dreyfuss ............... A61L 17/10 606/326 |
| 2007/0083236 A1 | 4/2007 | Sikora et al. |
| 2007/0135843 A1 | 6/2007 | Burkhart |
| 2007/0150003 A1 | 6/2007 | Dreyfuss et al. |
| 2007/0156148 A1 | 7/2007 | Fanton et al. |
| 2007/0156149 A1 | 7/2007 | Fanton et al. |
| 2007/0156150 A1 | 7/2007 | Fanton et al. |
| 2007/0156176 A1 | 7/2007 | Fanton et al. |
| 2007/0219557 A1 | 9/2007 | Bourque et al. |
| 2007/0219558 A1 | 9/2007 | Deutsch |
| 2007/0225719 A1 | 9/2007 | Stone et al. |
| 2007/0239209 A1 | 10/2007 | Fallman |
| 2007/0255317 A1 | 11/2007 | Fanton et al. |
| 2008/0009901 A1 | 1/2008 | Redmond et al. |
| 2008/0009904 A1 | 1/2008 | Bourque et al. |
| 2008/0027446 A1 | 1/2008 | Stone et al. |
| 2008/0065114 A1 | 3/2008 | Stone et al. |
| 2008/0077182 A1 | 3/2008 | Geissler et al. |
| 2008/0091237 A1 | 4/2008 | Schwartz et al. |
| 2008/0103528 A1 | 5/2008 | Zirps et al. |
| 2008/0140092 A1 | 6/2008 | Stone et al. |
| 2008/0147063 A1 | 6/2008 | Cauldwell et al. |
| 2008/0188893 A1 | 8/2008 | Selvitelli et al. |
| 2008/0195205 A1 | 8/2008 | Schwartz |
| 2008/0208253 A1 | 8/2008 | Dreyfuss et al. |
| 2008/0208265 A1 | 8/2008 | Frazier et al. |
| 2008/0228265 A1 | 9/2008 | Spence et al. |
| 2008/0255613 A1 | 10/2008 | Kaiser et al. |

(56) References Cited

U.S. PATENT DOCUMENTS

| | | |
|---|---|---|
| 2008/0275469 A1 | 11/2008 | Fanton et al. |
| 2008/0312689 A1 | 12/2008 | Denham et al. |
| 2009/0023984 A1 | 1/2009 | Stokes et al. |
| 2009/0036905 A1 | 2/2009 | Schmieding |
| 2009/0043317 A1 | 2/2009 | Cavanaugh et al. |
| 2009/0054928 A1 | 2/2009 | Denham et al. |
| 2009/0062850 A1 | 3/2009 | Ken |
| 2009/0062854 A1 | 3/2009 | Kaiser et al. |
| 2009/0082790 A1 | 3/2009 | Shad et al. |
| 2009/0082805 A1 | 3/2009 | Kaiser et al. |
| 2009/0082807 A1* | 3/2009 | Miller ............... A61B 17/0401 606/232 |
| 2009/0088798 A1 | 4/2009 | Snyder et al. |
| 2009/0099598 A1 | 4/2009 | McDevitt et al. |
| 2009/0138042 A1 | 5/2009 | Thal |
| 2009/0149883 A1 | 6/2009 | Brunsvold |
| 2009/0234387 A1 | 9/2009 | Miller et al. |
| 2009/0281568 A1 | 11/2009 | Cendan et al. |
| 2009/0281581 A1 | 11/2009 | Berg |
| 2009/0287246 A1 | 11/2009 | Cauldwell et al. |
| 2009/0306711 A1 | 12/2009 | Stone et al. |
| 2009/0312776 A1 | 12/2009 | Kaiser et al. |
| 2009/0312794 A1 | 12/2009 | Nason et al. |
| 2009/0318958 A1 | 12/2009 | Ochia |
| 2010/0004683 A1 | 1/2010 | Hoof et al. |
| 2010/0016892 A1 | 1/2010 | Kaiser et al. |
| 2010/0094425 A1 | 4/2010 | Bentley et al. |
| 2010/0162882 A1 | 7/2010 | Shakespeare |
| 2010/0204730 A1 | 8/2010 | Maiorino et al. |
| 2010/0249809 A1 | 9/2010 | Singhatat et al. |
| 2010/0249834 A1 | 9/2010 | Dreyfuss |
| 2010/0256677 A1 | 10/2010 | Albertorio et al. |
| 2010/0292732 A1 | 11/2010 | Hirotsuka et al. |
| 2010/0292792 A1 | 11/2010 | Stone et al. |
| 2011/0022083 A1 | 1/2011 | DiMatteo et al. |
| 2011/0022084 A1 | 1/2011 | Sengun et al. |
| 2011/0077667 A1 | 3/2011 | Singhatat et al. |
| 2011/0098727 A1 | 4/2011 | Kaiser et al. |
| 2011/0152928 A1 | 6/2011 | Colleran et al. |
| 2011/0190815 A1 | 8/2011 | Saliman |
| 2011/0208239 A1 | 8/2011 | Stone et al. |
| 2011/0208240 A1 | 8/2011 | Stone et al. |
| 2011/0213416 A1 | 9/2011 | Kaiser |
| 2011/0238111 A1 | 9/2011 | Frank |
| 2011/0264140 A1 | 10/2011 | Lizardi et al. |
| 2011/0264141 A1 | 10/2011 | Denham et al. |
| 2011/0270278 A1 | 11/2011 | Overes et al. |
| 2012/0046693 A1 | 2/2012 | Denham et al. |
| 2012/0053630 A1 | 3/2012 | Denham et al. |
| 2012/0059417 A1 | 3/2012 | Norton et al. |
| 2012/0101523 A1 | 4/2012 | Wert et al. |
| 2012/0101524 A1 | 4/2012 | Bennett |
| 2012/0130423 A1 | 5/2012 | Sengun et al. |
| 2012/0130424 A1 | 5/2012 | Sengun et al. |
| 2012/0150223 A1 | 6/2012 | Manos et al. |
| 2012/0296375 A1 | 11/2012 | Thal |
| 2013/0096611 A1 | 4/2013 | Sullivan |
| 2013/0110165 A1 | 5/2013 | Burkhart et al. |
| 2013/0158598 A1 | 6/2013 | Lizardi |
| 2013/0253581 A1 | 9/2013 | Robison |
| 2013/0261664 A1 | 10/2013 | Spenciner et al. |
| 2013/0296895 A1 | 11/2013 | Sengun |
| 2013/0296896 A1 | 11/2013 | Sengun |
| 2013/0296931 A1 | 11/2013 | Sengun |
| 2013/0296934 A1 | 11/2013 | Sengun |
| 2014/0039551 A1 | 2/2014 | Donahue |
| 2014/0081324 A1 | 3/2014 | Sengun |
| 2014/0107701 A1 | 4/2014 | Lizardi et al. |
| 2014/0188163 A1 | 7/2014 | Sengun |
| 2014/0188164 A1 | 7/2014 | Sengun |
| 2014/0277121 A1 | 9/2014 | Pilgeram et al. |
| 2014/0277132 A1 | 9/2014 | Sengun et al. |
| 2014/0330312 A1 | 11/2014 | Spenciner et al. |
| 2014/0343606 A1 | 11/2014 | Hernandez et al. |
| 2014/0343607 A1 | 11/2014 | Sengun et al. |
| 2015/0012038 A1 | 1/2015 | Sengun et al. |
| 2015/0025572 A1 | 1/2015 | Sengun |
| 2015/0045832 A1 | 2/2015 | Sengun |
| 2015/0238183 A1 | 8/2015 | Sengun |
| 2015/0245832 A1 | 9/2015 | Sengun |
| 2015/0297214 A1 | 10/2015 | Hernandez et al. |
| 2015/0313587 A1 | 11/2015 | Lizardi et al. |
| 2016/0128687 A1 | 5/2016 | Sengun |
| 2016/0278761 A1 | 9/2016 | Sengun et al. |
| 2016/0296222 A1 | 10/2016 | Sengun |
| 2017/0000479 A1 | 1/2017 | Sengun et al. |
| 2017/0303913 A1 | 10/2017 | Sengun et al. |
| 2017/0360428 A1 | 12/2017 | Sengun |
| 2017/0367690 A1 | 12/2017 | Sengun |
| 2018/0042600 A1 | 2/2018 | Hernandez et al. |
| 2018/0098763 A1 | 4/2018 | Spenciner et al. |
| 2018/0140292 A1 | 5/2018 | Sengun et al. |
| 2019/0216457 A1 | 7/2019 | Sengun |
| 2019/0223857 A1 | 7/2019 | Sengun |
| 2019/0223860 A1 | 7/2019 | Sengun et al. |
| 2020/0178952 A1 | 6/2020 | Sengun |
| 2020/0383681 A1 | 12/2020 | Sengun et al. |
| 2021/0030411 A1 | 2/2021 | Spenciner et al. |
| 2021/0038214 A1 | 2/2021 | Sengun |
| 2021/0093312 A1 | 4/2021 | Hernandez et al. |
| 2021/0145433 A1 | 5/2021 | Sengun et al. |
| 2021/0282763 A1 | 9/2021 | Sengun et al. |
| 2022/0167959 A1 | 6/2022 | Sengun |
| 2022/0296229 A1 | 9/2022 | Sengun |
| 2023/0112112 A1 | 4/2023 | Sengun |
| 2023/0135885 A1 | 5/2023 | Snyder et al. |
| 2023/0240674 A1 | 8/2023 | Sengun et al. |

FOREIGN PATENT DOCUMENTS

| | | |
|---|---|---|
| CA | 2772500 C | 4/2018 |
| CN | 2719234 Y | 8/2005 |
| CN | 101252887 A | 8/2008 |
| CN | 101961256 A | 2/2011 |
| CN | 101442944 B | 6/2011 |
| CN | 101961257 B | 10/2015 |
| CN | 102113901 B | 8/2016 |
| CN | 102551824 B | 9/2016 |
| EP | 0706779 B1 | 5/2000 |
| EP | 0870471 B1 | 6/2003 |
| EP | 1568326 B1 | 10/2007 |
| EP | 1199035 B1 | 2/2008 |
| EP | 1707127 B1 | 12/2010 |
| EP | 2572650 A1 | 3/2013 |
| EP | 2662032 B1 | 10/2015 |
| EP | 2455004 B1 | 12/2016 |
| EP | 2277457 B1 | 1/2019 |
| EP | 2455003 B1 | 6/2021 |
| JP | S6290148 A | 4/1987 |
| JP | H067422 A | 1/1994 |
| JP | H08206122 A | 8/1996 |
| JP | 2000512193 A | 9/2000 |
| JP | 2003528648 A | 9/2003 |
| JP | 2005237966 A | 9/2005 |
| JP | 2006516468 A | 7/2006 |
| JP | 2007075616 A | 3/2007 |
| JP | 2008514382 A | 5/2008 |
| JP | 2008543509 A | 12/2008 |
| JP | 2009522065 A | 6/2009 |
| JP | 2010521195 A | 6/2010 |
| JP | 2011025034 A | 2/2011 |
| JP | 2012110711 A | 6/2012 |
| JP | 2012110712 A | 6/2012 |
| WO | 1995019139 A1 | 7/1995 |
| WO | 1997017901 A1 | 5/1997 |
| WO | 1998011825 A1 | 3/1998 |
| WO | 1998042261 A1 | 10/1998 |
| WO | 2001006933 A2 | 2/2001 |
| WO | 2003022161 A1 | 3/2003 |
| WO | 2007002561 A1 | 1/2007 |
| WO | 2007005394 A1 | 1/2007 |
| WO | 2007078281 A2 | 7/2007 |
| WO | 2007109769 A1 | 9/2007 |

(56) References Cited

FOREIGN PATENT DOCUMENTS

| WO | 2009107121 A2 | 9/2009 |
| WO | 2010028324 A2 | 3/2010 |
| WO | 2010105046 A1 | 9/2010 |

OTHER PUBLICATIONS

End Definition Meaning & Dictionary.com, https://www.dictionary.com/browse/end accessed Nov. 23, 2024 (Year: 2024).*
[No Author Listed] Arthex is Reaching New Heights In Rotar Cuff Repair. Arthex Inc. 2007. 8 pages.
[No Author Listed] Arthroscopic Knot Tying Manual 2005. DePuy Mitek. 27 pages.
[No Author Listed] Gryphon Brochure. DePuy Mitek. 2 pages (undated).
[No Author Listed] Versalok Anchor. Brochure. DePuy Mitek, a Johnson & Johnson company, 92 pages, 2007.
Adjacent Definition & Meaning, https://www.dictionary.com/browse/adjacent, copyright 2022 Dictionary.com, LLC (Year: 2022).
Allcock, The Encyclopedia of Polymer Science, vol. 13, pp. 31-41, Wiley Intersciences, John Wiley & Sons, 1988.
Anchor Definition & Meaning, Merriam-Webster, https://www.merriam-webster.com/dictionary/anchor; copyright 2022 Merriam-Webster, Incorporated (Year: 2022).
Chinese Office Action for Application No. 201310163420.7, issued May 5, 2016 (21 pages).
Chinese Office Action for Application No. 201310163700.8 issued Jun. 3, 2016 (14 pages).
Chinese Office Action for Application No. 201310429109.2 issued Oct. 24, 2016 (13 pages).
Chinese Office Action for Application No. 201310741440.8, issued Jan. 26, 2017 (12 pages).
Cohn et al., Biodegradable PEO/PLA block copolymers. J Biomed Mater Res. Nov. 1988;22(11):993-1009.
Cohn et al., Polym Preprint. 1989;30(1):498.
Dahl et al., Biomechanical characteristics of 9 arthroscopic knots. Arthroscopy. Jun. 2010;26(6):813-8.
EP Search Report for Application No. 11190157.5 issued Feb. 27, 2012. (8 pages).
Extended European Search Report for Application No. 11190157.5 issued Jul. 6, 2012. (10 pages).
EP Search Report for Application No. 11190159.1 issued Feb. 21, 2012. (8 pages).
Extended European Search Report for Application No. 11190159.1 issued Jul. 6, 2012. (11 pages).
Extended European Search Report for Application No. 11195100.0 issued Oct. 17, 2012. (7 pages).
Extended European Search Report for Application No. 13166905.3 issued Aug. 13, 2013 (9 pages).
Extended European Search Report for Application No. 13166907.9, issued Aug. 1, 2013 (6 pages).
Extended European Search Report for Application No. 13166908.7, issued Aug. 23, 2013 (8 pages).
Extended European Search Report for Application No. 13185425.9 issued Dec. 16, 2013 (9 pages).
Extended European Search Report for Application No. 13199724.9 issued Apr. 4, 2014 (6 pages).
Extended European Search Report for Application No. 16205548.7, issued Dec. 22, 2017 (11 pages).
Extended European Search Report for Application No. 21178450.9, issued Oct. 11, 2021.
Extended European Search Report for Application No. 21178549.0, issued Nov. 17, 2021 (22 pages).
Extended European Search Report for Application No. 21178459.0, issued Nov. 17, 2021 (22 pages).
Google dictionary definition of the term "Tube" retrieved Nov. 24, 2019 (Year: 2019).
Heller, Handbook of Biodegradable Polymers, edited by Domb, et al., Hardwood Academic Press, pp. 99-118 (1997).
Indian First Examination Report for Application No. 3243/DEL/2011, issued Dec. 30, 2019 (6 pages).
International Search Report for Application No. PCT/US2011/067119, mailed Jun. 4, 2012. (6 pages).
Japanese Office Action for Application No. 2011-281088, issued Nov. 10, 2015 (4 pages).
Japanese Office Action for Application No. 2013546447, issued Nov. 17, 2015 (3 pages).
Japanese Office Action for Application No. 2013-097645, mailed May 9, 2017 (6 pages).
Japanese Office Action for Application No. 2013-268840, mailed Sep. 26, 2017 (5 pages).
Kemnitzer et al., Handbook of biodegradable Polymers. Eds. Domb et al. Hardwood Acad. Press. 1997;251-72.
Vandorpe et al., Handbook of Biodegradable Polymers, edited by Domb, et al., Hardwood Acad. Press, pp. 161-182 (1997).

* cited by examiner

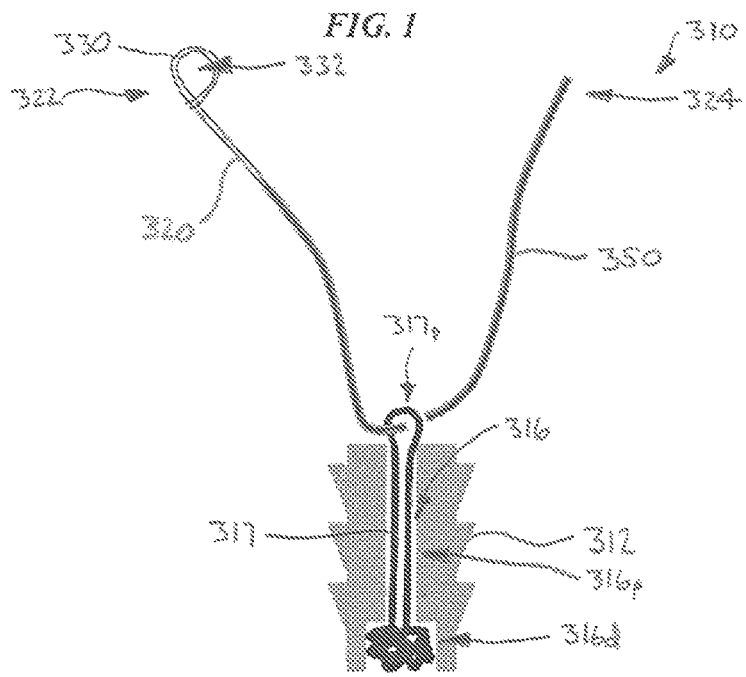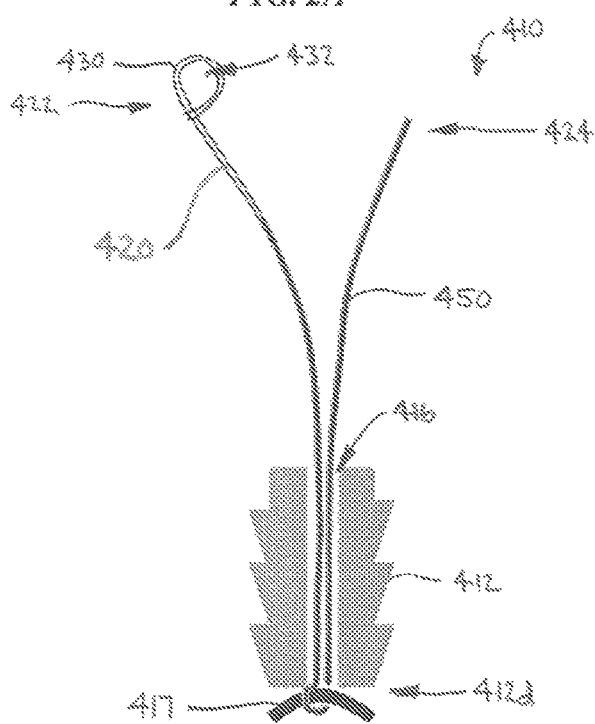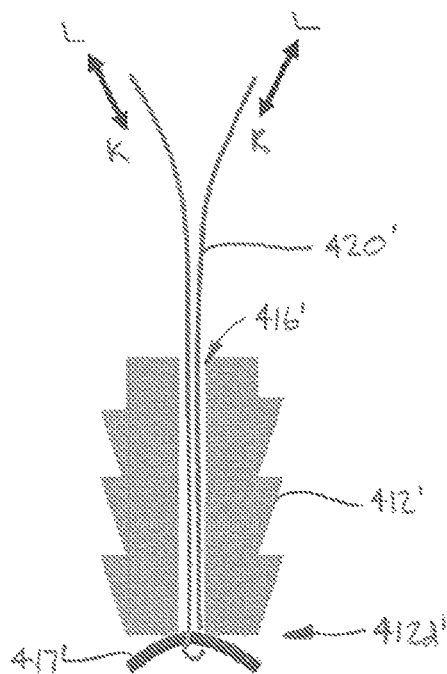

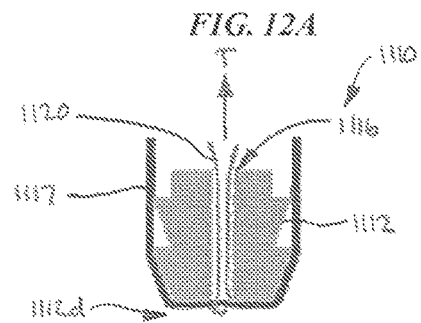
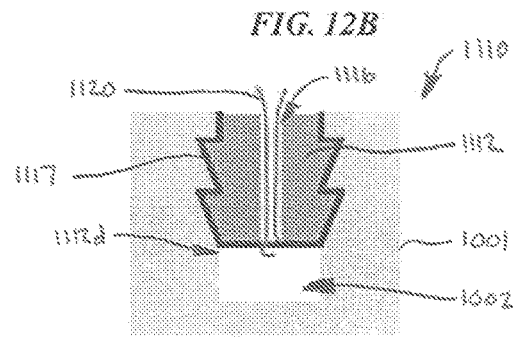
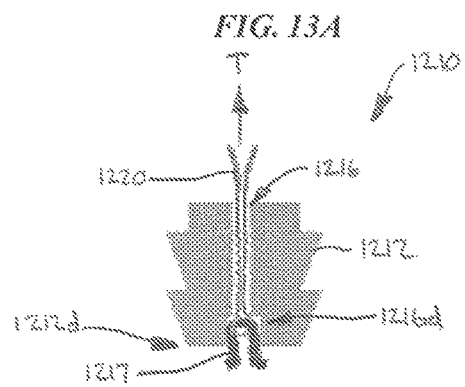
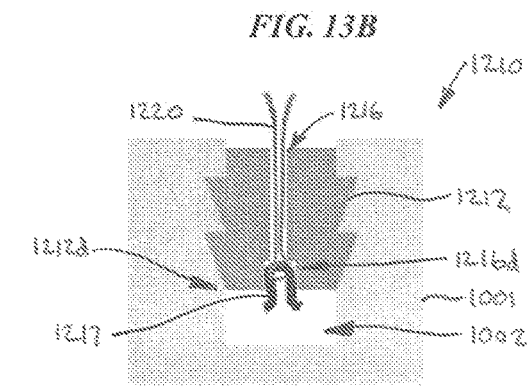
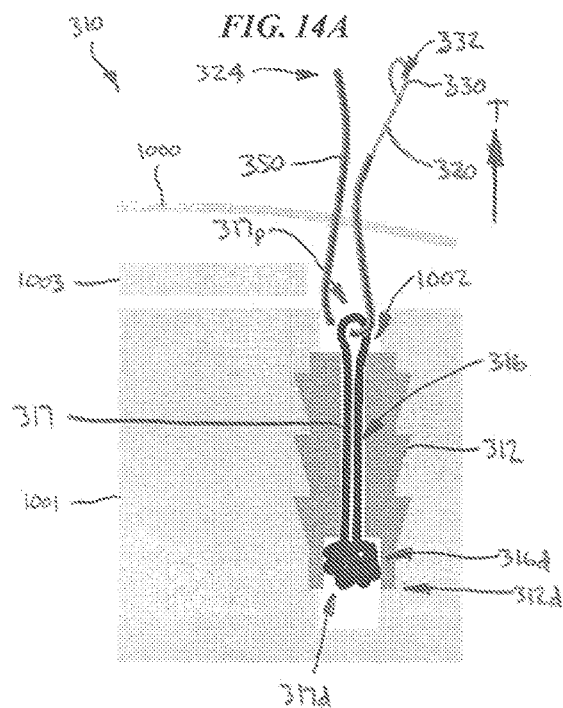
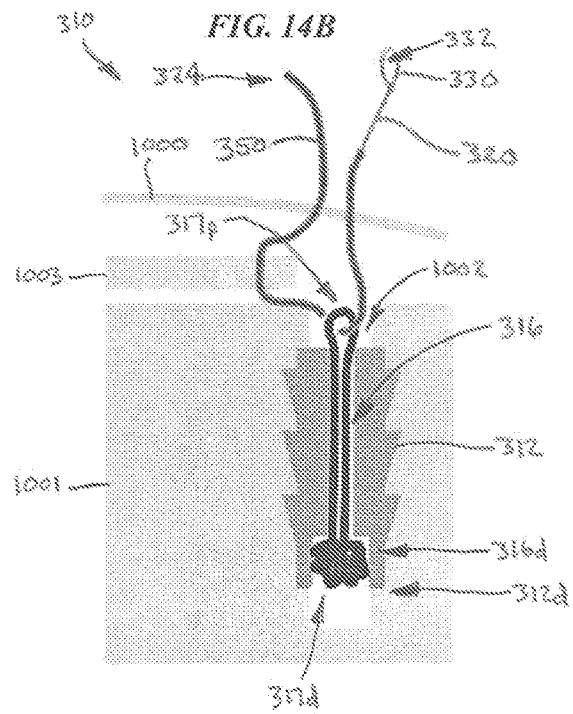

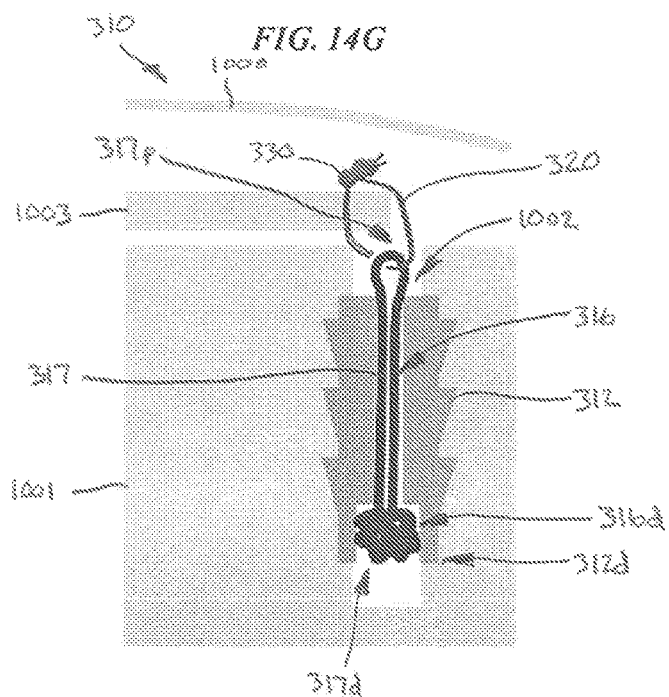
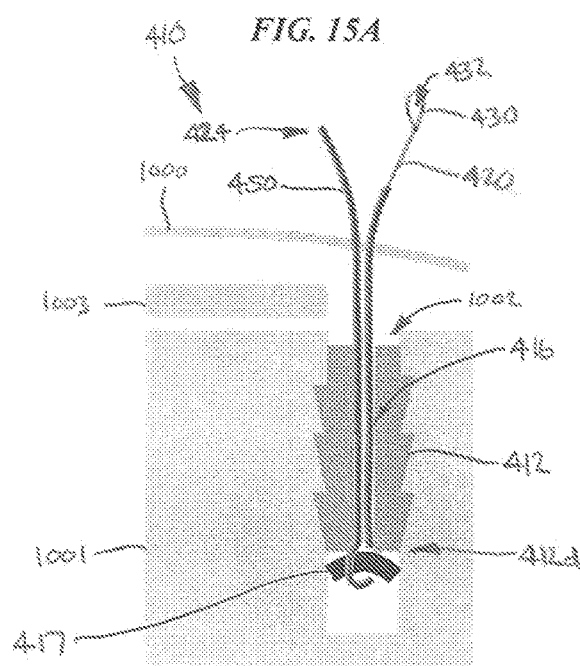
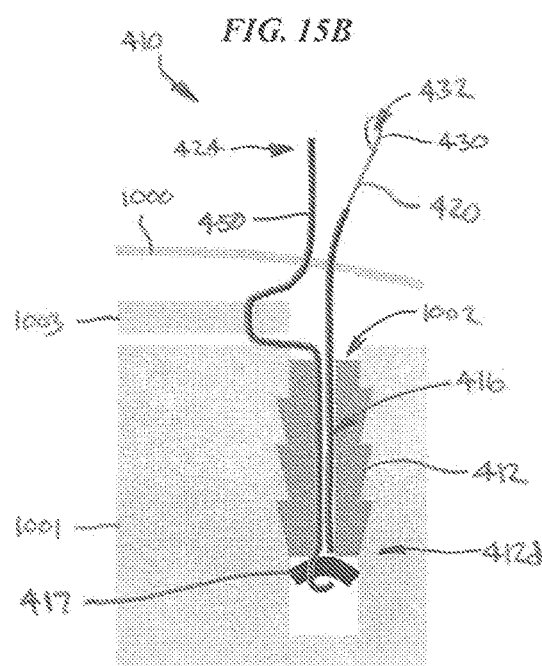

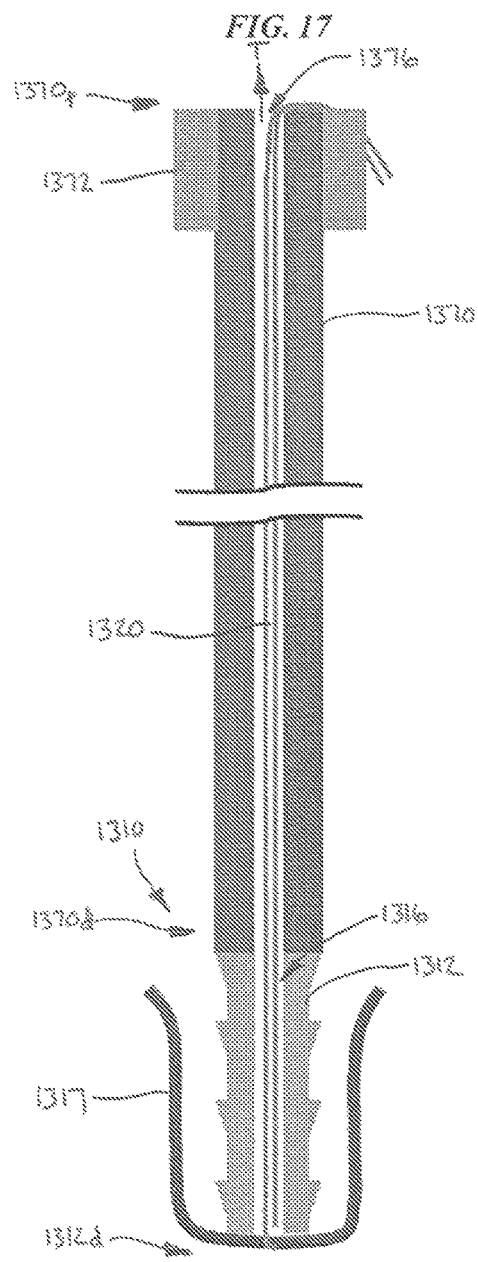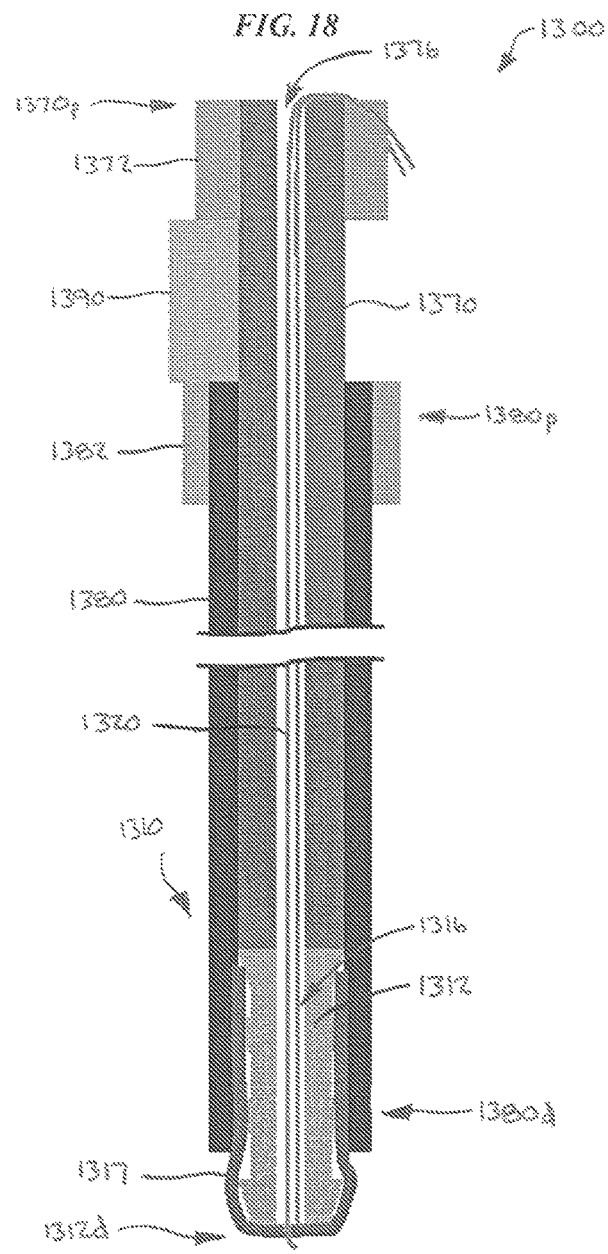

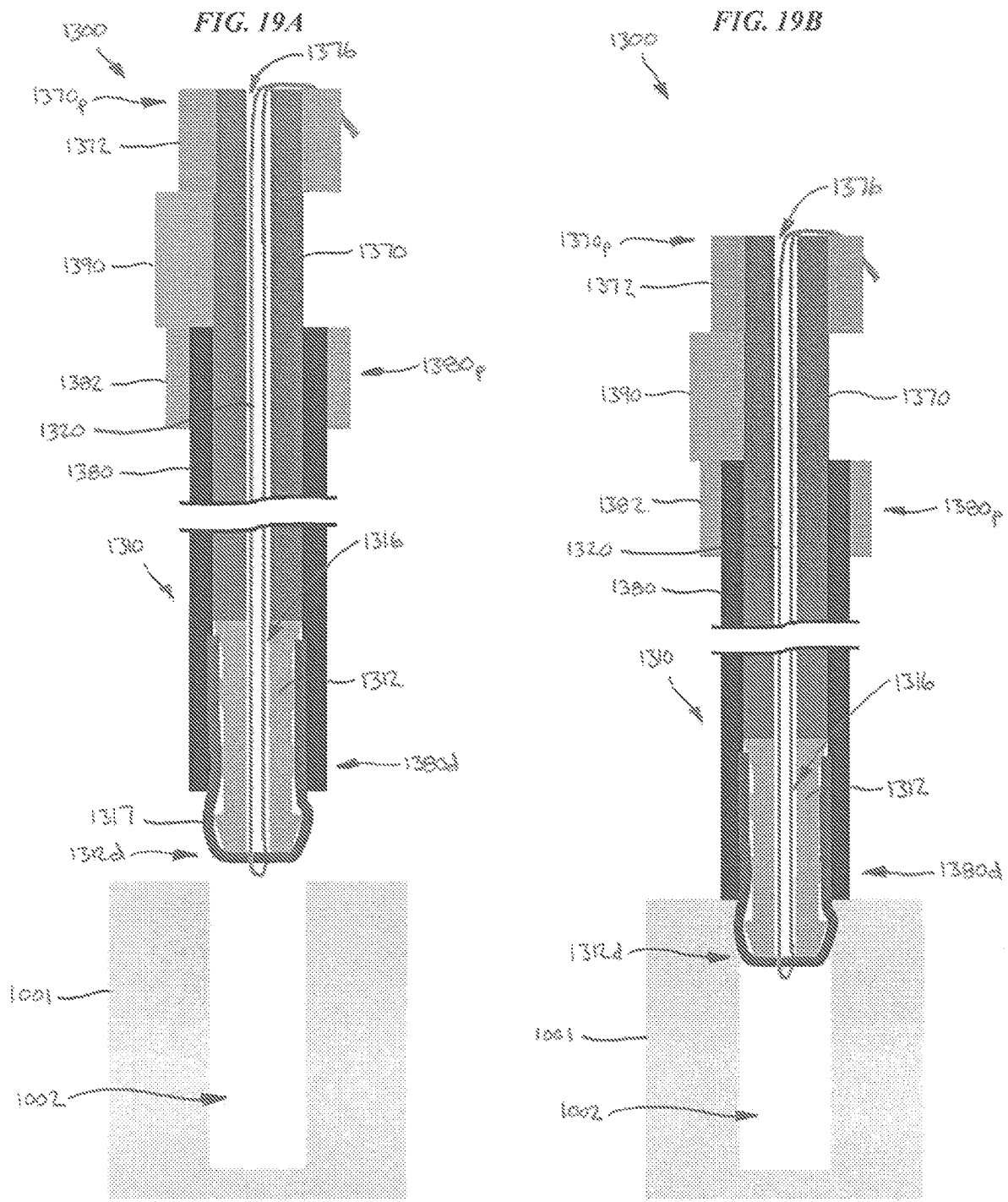

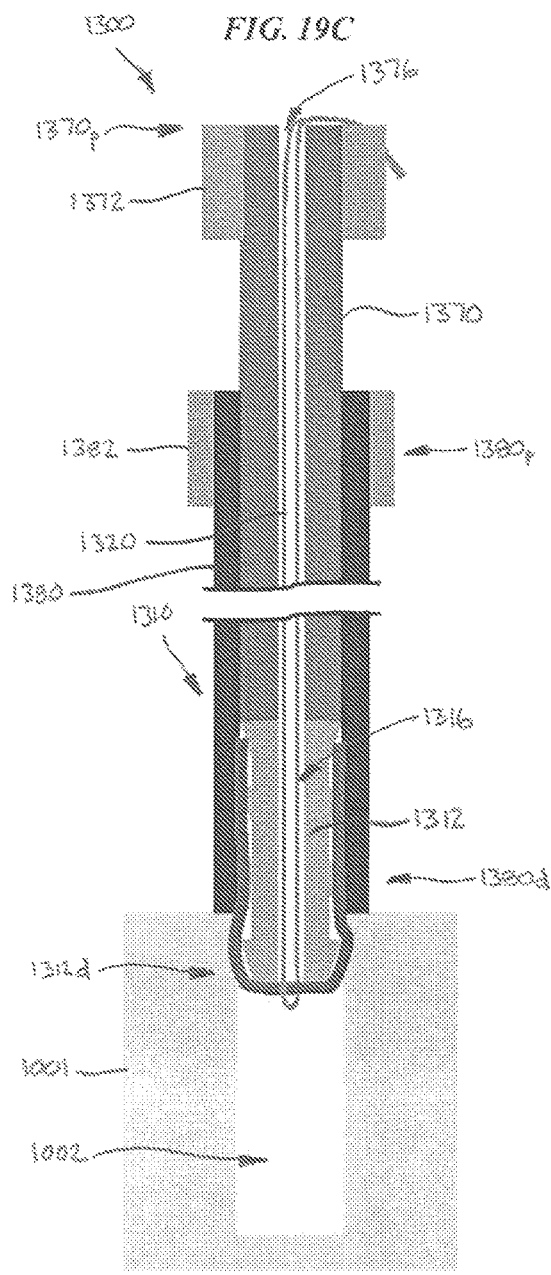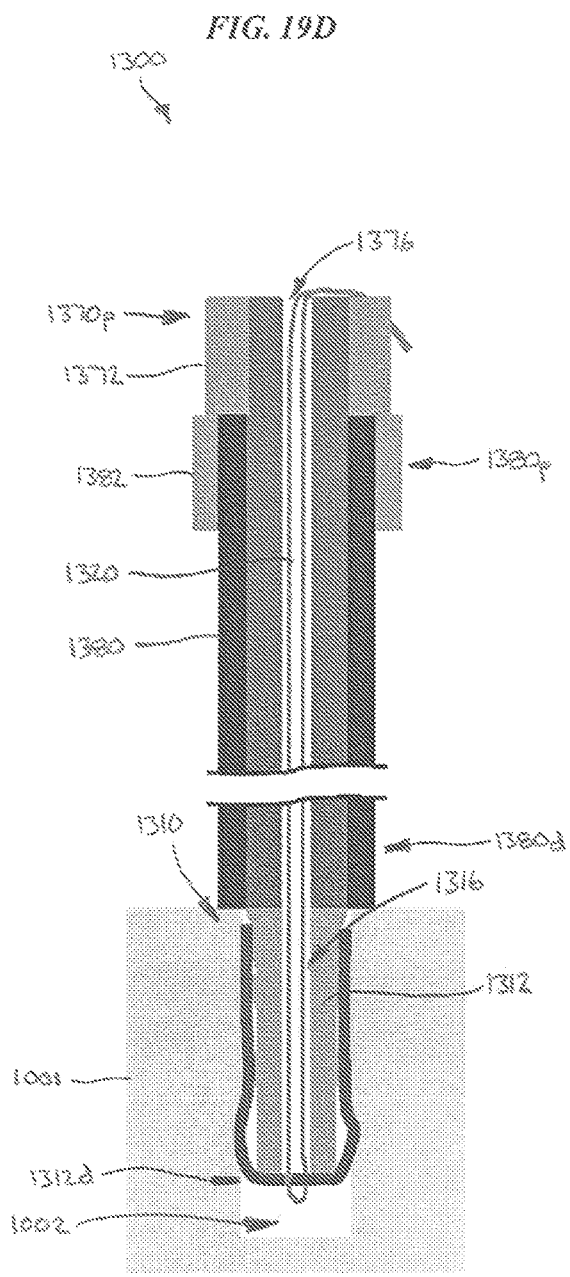

SYSTEMS, DEVICES, AND METHODS FOR SECURING TISSUE USING HARD ANCHORS

CROSS-REFERENCE TO RELATED APPLICATION

The present application is a continuation of and claims priority to U.S. patent application Ser. No. 16/887,683, filed May 29, 2020, and entitled "Systems, Devices, and Methods for Securing Tissue Using Hard Anchors," which is a continuation of and claims priority to U.S. patent application Ser. No. 15/692,885, filed Aug. 31, 2017, entitled "Systems, Devices, and Methods for Securing Tissue Using Hard Anchors," and which issued as U.S. Pat. No. 10,695,047 on Jun. 30, 2020, which is a continuation of and claims priority to U.S. patent application Ser. No. 13/623,429, filed Sep. 20, 2012, entitled "Systems, Devices, and Methods for Securing Tissue Using Hard Anchors," and which issued as U.S. Pat. No. 9,763,655 on Sep. 19, 2017, the contents of each which is hereby incorporated by reference herein in their entireties.

FIELD

The present disclosure relates to systems, devices, and methods for securing soft tissue to bone, and more particularly relates to securing soft tissue using rigid or hard anchors in conjunction with a combination of surgical filaments to minimize trauma during surgical procedures.

BACKGROUND

A common injury, especially among athletes and people of advancing age, is the complete or partial detachment of tendons, ligaments, or other soft tissues from bone. Tissue detachment may occur during a fall, by overexertion, or for a variety of other reasons. Surgical intervention is often needed, particularly when tissue is completely detached from its associated bone. Currently available devices for tissue attachment include screws, staples, suture anchors, and tacks. Currently available devices for patients of advancing age can be particularly insufficient due to soft and weak bones leading to inadequate fixation between the anchor and bones and the anchors and filaments with which the anchors are coupled.

Anchors and repair filaments are typically used in soft tissue repair procedures to secure the tissue in a desired location. Smaller anchors can be helpful in minimizing trauma associated with creating surgical openings for accessing the location for soft tissue repair, and for minimizing trauma associated with implanting the anchor in bone as part of the tissue repair procedure. Because anchors are often disposed in holes that are pre-formed in bone, the smaller an anchor is, the smaller a pre-formed hole can be. The anchors can include repair filaments coupled thereto and the repair filaments can be coupled to the soft tissue and operable to draw the soft tissue closer to the bone in which the anchor is implanted. A number of challenges, however, present themselves when using small anchors coupled with repair filaments for soft tissue repair. For example, despite their size, small anchors and repair filaments are limited in their abilities to withstand both high levels of load that result from tissue and bone movement after the procedure is completed and high levels of load that can occur while the procedure is being performed. Additionally, the small anchors and repair filaments can be susceptible to undesirably sliding therebetween both during and after the procedure. Likewise, the repair filaments can be susceptible to undesirably fraying or breaking, for instance at locations where the repair filament is coupled to the anchor.

It can also be desirable to minimize the number of knots used in conjunction with the repair filament when performing soft tissue repair procedures. A variety of different knots, such as sliding knots, can be used to help draw and secure soft tissue with respect to bone. Although the tying of knots at a surgical site is common, in some instances knots can have a tendency to slip, which in turn can cause a loss of tension between the tissue and bone. This drawback is sometimes referred to as a loss of "loop security." In addition to this "loop security" issue, conventional knots typically have an overall size that can be obstructive or intrusive, especially in tight joints, which may damage cartilage or other tissue by abrasion with the knot.

It is therefore desirable to provide systems, devices, and methods that reduce the amount of trauma associated with using hard or rigid anchors during soft tissue repair procedures while maintaining or improving the holding strength such systems, devices, and methods can provide. It is also desirable to provide systems, devices, and methods for use in soft tissue repair that minimize or eliminate the number and size of knots to be tied by a surgeon, particularly during arthroscopic repair procedures.

SUMMARY

Systems, devices, and methods are generally provided for securing soft tissue to bone. In one exemplary embodiment a surgical soft tissue repair device includes an anchor, a repair filament, and a connecting filament in sliding engagement with the repair filament. The anchor can be configured to be fixated in bone and can have at least one bore extending therethrough. The connecting filament can have a folded configuration in which the connecting filament is unable to pass through the bore and can be effective to connect the repair filament to the anchor. In some embodiments the anchor can be a rigid anchor. Further, in some embodiments the repair filament can include a snare assembly having a collapsible snare at one end and a terminal end opposite the collapsible snare. The anchor can be positioned at an intermediate location on the repair filament between the collapsible snare and the terminal end.

The bore of the anchor can be an axial bore, or alternatively, it can be a transverse bore. In an embodiment in which the bore is an axial bore, the bore can be stepped such that there is a first, smaller diameter at a proximal end of the bore and a second, greater diameter at a distal end of the bore. The connecting filament can include at least one of a continuous loop and a knot. In some embodiments the repair filament can slidably engage with the connecting filament by passing through the connecting filament. In some other embodiments the connecting filament can be held by the anchor and/or an insertion tool. In still other embodiments the connecting filament does not couple to the anchor. The connecting filament can have a first configuration in which it is able to pass through the bore of the anchor and a second configuration in which it is unable to pass through the bore of the anchor, thereby being effective to secure the repair filament to the anchor. An insertion tool can be removably coupled to the anchor. The insertion tool can have at least one bore extending therethrough with its bore being substantially aligned with the bore of the anchor.

One exemplary embodiment of a surgical repair method includes inserting an anchor into a hole in a bone at a location proximate to detached soft tissue. The anchor can have a bore extending therethrough and the anchor can be coupled to a snare assembly by a connecting filament that is disposed in or adjacent to the bore at a position distal to the snare assembly. The snare assembly can have a collapsible snare at one end and at least one elongate filament extending therefrom. The elongate filament can have a terminal end opposite the collapsible snare. The method can also include passing at least one of the snare and the terminal end of the elongate filament through at least a portion of the detached tissue, inserting the terminal end of the elongate filament through the snare, collapsing the snare around the elongate filament, and sliding the collapsed snare toward the soft tissue to apply tension to the filament between the anchor and the tissue to bring the tissue into proximity with the bone. The connecting filament can be slidably coupled to the repair filament approximately at or adjacent to a distal end of the anchor. In some embodiments, the method can further include actuating the connecting filament to move from a first configuration in which it is able to pass through the bore of the anchor to a second configuration in which it is unable to pass through the bore of the anchor and is effective to secure the repair filament to the anchor.

In some embodiments at least a portion of the connecting filament can be disposed within the bore. In some other embodiments at least a portion of the repair filament can be disposed within the bore and the connecting filament can be disposed on a side of the bore opposite to the snare assembly. The method can also include tensioning the repair filament to configure the connecting filament in a connecting configuration in which the connecting filament is unable to pass through the bore to fix tissue relative to the bone.

BRIEF DESCRIPTION OF DRAWINGS

This invention will be more fully understood from the following detailed description taken in conjunction with the accompanying drawings, in which:

FIG. 1 is a schematic view of one exemplary embodiment of a surgical soft tissue repair device;

FIG. 2A is a schematic view of another exemplary embodiment of a surgical soft tissue repair device;

FIG. 2B is a schematic view of still another exemplary embodiment of a surgical soft tissue repair device;

FIG. 12A is a schematic view of yet another exemplary embodiment of a surgical soft tissue repair device that includes an anchor, a repair filament, and yet another exemplary embodiment of a connecting filament configuration for coupling the repair filament to the anchor;

FIG. 12B is a schematic view of the surgical soft tissue repair device of FIG. 12A disposed in bone;

FIG. 13A is a schematic view of another exemplary embodiment of a surgical soft tissue repair device that includes an anchor, a repair filament, and another exemplary embodiment of a connecting filament configuration for coupling the repair filament to the anchor;

FIG. 13B is a schematic view of the surgical soft tissue repair device of FIG. 13A disposed in bone;

FIGS. 14A-14G are sequential views of one exemplary embodiment for using the surgical soft tissue repair device of FIG. 1 to secure tissue to bone;

FIGS. 15A-15G are sequential views of one exemplary embodiment for using the surgical soft tissue repair device of FIG. 2A to secure tissue to bone;

FIG. 17 is a schematic view of the surgical soft tissue repair device of FIG. 16 coupled to an insertion tool;

FIG. 18 is a schematic view of an insertion assembly that includes the surgical soft tissue repair device and insertion tool of FIG. 17, as well as a guide portion and spacer element; and FIGS. 19A-19E are sequential views of one exemplary embodiment for using the insertion assembly of FIG. 18 to secure tissue to bone.

DETAILED DESCRIPTION

Figure 3:
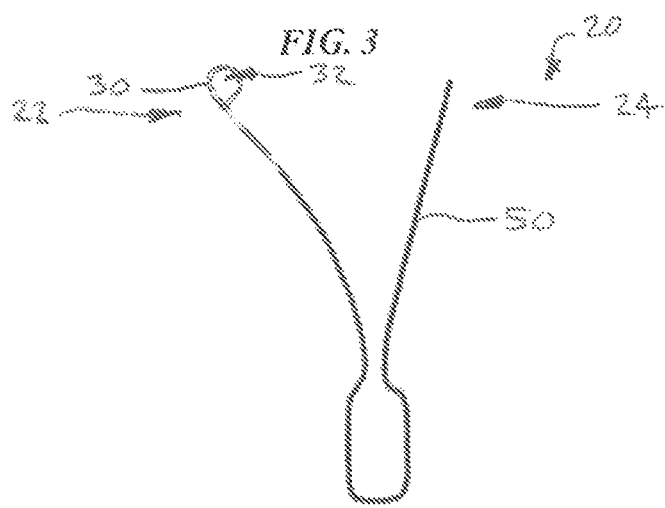
FIG. 3 is a schematic view of one exemplary embodiment of a snare assembly for use as a repair filament of a surgical soft tissue repair device.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention. Further, in the present disclosure, like-numbered components of the embodiments generally have similar features. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

The figures provided herein are not necessarily to scale. Still further, to the extent arrows are used to describe a direction of movement, these arrows are illustrative and in no way limit the direction the respective component can or should be moved. A person skilled in the art will recognize other ways and directions for creating the desired result. Additionally, a number of terms may be used throughout the disclosure interchangeably but will be understood by a person skilled in the art. By way of non-limiting example, the terms suture, filament, and flexible members may be used interchangeably.

Systems, devices, and methods for soft tissue repair are generally provided and they generally involve the use of surgical filaments and/or flexible members in conjunction with hard or rigid anchors. Surgical repair filaments, which are flexible members that can come in a variety of configurations, are used in connection with anchors to attach or reattach soft tissue to bone. The repair filaments can pass through soft tissue so that the soft tissue can be positioned in a desired location. The repair filaments are secured to anchors which, in turn, are fixed in bone. In one aspect of the invention, the anchors have one or more lumens or bores extending therethrough for receiving all or part of the repair filament. In a further aspect, the lumens or bores of the anchor have a diameter that is slightly larger than a width formed by a repair filament such that the lumen or bore is barely able to accommodate the repair filament. In some embodiments the width formed by the repair filament can be the equivalent of a diameter of the repair filament, while in some other embodiments the width formed by the repair filament can be the equivalent of approximately two diameters of the repair filament, for instance when at least a portion of a loop of repair filament is disposed in the lumen or bore of the anchor. A configuration in which the lumen or bore of the anchor is barely able to accommodate the repair filament can allow the repair filament to slide with respect to the anchor while still preventing the repair filament from easily falling out of the bore or lumen.

The repair filament can interface with the anchor and connect thereto with the aid of a connecting filament. In some embodiments, the repair filament and the connecting filament can be in sliding engagement approximately at or adjacent to a distal end of the anchor. The connecting filament is such that it has a diameter, either in a normal configuration or an altered configuration, that is greater than the diameter of the lumen or bore. When the connecting filament is in an altered configuration, such as a folded configuration, the connecting filament can be unable to pass through the bore. The connecting filament can render a rigid engagement member, such as a cross-bar or eyelet, unnecessary. Further, the repair filament is able to couple to the connecting filament in such a way that provides a secure connection between the repair filament, the anchor, and soft tissue that is to be repaired or reattached. While in some embodiments at least a portion of the repair filament can extend substantially through the bore, in other embodiments a portion of the connecting filament extends proximally through the bore of the anchor and couples with the repair filament at a proximal side of the anchor. In such embodiments, the lumens or bores of the anchor have a diameter that is slightly larger than a width formed by a connecting filament such that the lumen or bore is barely able to accommodate the connecting filament. This configuration prevents the connecting filament from easily falling out of the bore or lumen while still allowing the repair filament to slide with respect to the anchor.

One beneficial aspect of the devices and systems described herein is that the use of relatively small anchor devices is possible, while maintaining the ability to use a high strength repair filament and anchor system that can withstand high loads. The use of a soft and flexible connecting filament is also advantageous in that it enables the use of smaller anchors and provides for an interface between the anchor and repair filament that reduces trauma to the patients as well as the risk of damage to the repair filament. Further, the repair filament is able to slide relative to the connecting filament without damaging either component and while minimizing the risk of undesirable slippage between the repair filament and the anchor, and in turn between the soft tissue and bone attached thereto. The devices and systems provided herein allow for both improved and new procedures for soft tissue repair, and can be used in a number of different types of surgical procedures, including by way of non-limiting examples rotator cuff and instability repair procedures and other types of tendon and tissue repair procedures.

Soft Tissue Repair Devices

FIGS. 1, 2A, and 2B illustrate exemplary embodiments of surgical soft tissue repair devices that can be used to perform soft tissue repairs. Each includes a hard or rigid anchor for implantation into bone, a repair filament for coupling to soft tissue and drawing the soft tissue toward the bone in which the anchor is implanted, and a connecting filament for associating the repair filament with the anchor. Using soft and flexible components like a connecting filament in conjunction with repair filaments and hard anchors can be beneficial at least because it provides for a strong fixation in bone with additional flexibility in the design while minimizing the risk of trauma to the patient and damage to the repair filament.

FIG. 1 illustrates one exemplary embodiment of a surgical soft tissue repair device 310 that includes a hard or rigid anchor 312, a repair filament 320, and a connecting filament 317 that couples the repair filament 320 to the anchor 312. As shown, the anchor 312 includes an axial bore 316 formed therethrough and the connecting filament 317 is disposed through the bore 316 and is configured to couple to the repair filament 320 such that the anchor 312 is at an intermediate location on the repair filament 320. While the anchor and any associated bores and lumens can have a variety of configurations, in the illustrated embodiment the bore 316 is stepped such that a distal end 316d of the bore 316 has a diameter that is greater than a more proximal portion 316p of the bore 316. In other embodiments the bore 316 can have a constant diameter. In the illustrated embodiment the diameter of the proximal portion 316p is sized such that it is slightly larger than a width formed by the connecting filament 317 such that the bore 316 is barely able to accommodate the connecting filament 317. As shown, the width formed by the connecting filament 317 is approximately two diameters of the filament 317 due to the filament 317 having a looped configuration within the bore 316.

The repair filament can have a variety of configurations and constructions, including as simple as being an elongate flexible member or suture filament. However, in one embodiment the repair filament 320 can be a snare assembly having a collapsible snare 330 formed on a first end 322 and a terminal end 324 opposite the first end 322, with an intermediate portion extending therebetween. In some embodiments a sleeve 350 can be disposed around at least a portion of the repair filament 320. The terminal end 324 can be configured to pass through an opening 332 in the snare 330 to create a tensionable construct so that the snare assembly can draw two or more objects, such as tissue and bone, closer together, as described in greater detail below with respect to FIGS. 14A-15G.

The connecting filament 317 can be effective to connect the repair filament 320 and the anchor 312 in a way that minimizes the potential for damage to the repair filaments. As shown, a distal end 317d of the connecting filament 317 can be configured to have a diameter that is greater than the diameter of the bore 316, either in its natural state or in certain anchoring configurations that can result, for instance, from actuation initiated by a surgeon. In some embodiments the diameter of the distal end 317d of the connecting filament 317 remains approximately constant and it has dimensions that prevent its passage proximal of the distal end 316d of the bore 316. In other embodiments the distal end 317d can be actuated (e.g., by tension) to transition from an unstressed configuration in which the connecting filament 317 could fully pass through the bore 316 and an anchoring configuration in which the diameter of the connecting filament 317 increases to a size that prevents its passage through the bore 316. Accordingly, the connecting filament 317 is configured or configurable to be unable to pass through the bore 316. A person skilled in the art will recognize configurations of a connecting filament that can be used to allow a connecting filament to move from a first, unstressed configuration to a second, anchoring configuration. Some non-limiting examples of filaments that can move between these two configurations and which can be adapted for use as a connecting filament in conjunction with the teachings herein are described in greater detail in U.S. patent application Ser. No. 13/465,376 filed May 7, 2012, and entitled "Systems, Devices, and Methods for Securing Tissue Using Snare Assemblies and Soft Anchors," the content of which is incorporated by reference herein in its entirety. A proximal end 317p of the connecting filament 317 can be configured to couple to the repair filament 320, which in the illustrated embodiment is accomplished by looping the repair filament 320 through a loop in the proximal end 317p of the connecting filament 317. A person skilled in the art will recognize a number of different ways by which the repair filament 320 can be coupled to the connecting filament 317, including by passing one filament through the other.

FIG. 2A illustrates another exemplary embodiment of a surgical soft tissue repair device 410 in which a repair filament 420 is a snare assembly similar to the snare assembly of FIG. 1 in that it includes a collapsible snare 430 formed on a first end 422, a terminal end 424 opposite the first end 422, the terminal end 424 being configured to pass through an opening 432 in the snare 430 to create a tensionable construct, and an optional sleeve 450 disposed around at least a portion of the repair filament 420. The repair filament 420 is coupled to the hard anchor 412 by way of a flexible connecting filament 417 disposed on a distal side 412d of the anchor 412 such that the anchor 412 is at an intermediate location on the repair filament 420. As shown, the connecting filament 417 is in sliding engagement with the repair filament 420 approximately at or adjacent to the distal end 412d of the anchor 412. FIG. 2B illustrates an exemplary embodiment of a surgical soft tissue repair device 410' that is similar to the surgical repair device 410 of FIG. 2A except the repair filament 420' is not a snare assembly but is instead an elongate filament having proximal and distal ends. The repair filament 420' is coupled to a hard anchor 412' having a flexible connecting filament 417' associated therewith at a distal end 412d' thereof such that the anchor 412' is at an intermediate location on the repair filament 420'. As shown, the connecting filament 417' is in sliding engagement with the repair filament 420' approximately at or adjacent to the distal end 412d' of the anchor 412'. The repair filament 420' can be slidably coupled to the flexible connecting filament 417' such that it can move distally approximately in a direction K and proximally approximately in a direction L as illustrated by the arrows in FIG. 2B. Although FIGS. 2A and 2B illustrate the engagement between the repair filament 420, 420' and the connecting filament 417, 417' to be approximately at or distal to the distal end 412d, 412d' of the anchor 412, 412', it is understood that tension applied to the repair filament 420, 420' can cause the location of the engagement between the two filaments to shift proximally to a position slightly adjacent to the distal end 412d, 412d'.

The anchor 412, 412' can include an axial bore 416, 416' formed therethrough and the repair filament 420, 420' can be disposed through the bore 416, 416' to couple to the connecting filament 417, 417'. The connecting filament 417, 417' can be effective to connect the repair filament 420, 420' and the anchor 412, 412'. As shown, the connecting filament 417, 417' can be configured such that in an approximately folded configuration the connecting filament 417, 417' is unable to pass through the bore 416, 416' because a width formed when two portions of the connecting filament 417, 417' are compressed together is greater than the diameter of the bore 416, 416', thus anchoring the repair filament 420, 420' with respect to the anchor 412, 412'. The diameter of the bore 416, 416' is sized such that it is slightly larger than the width formed by the repair filament 420, 420' such that the bore 416, 416' is barely able to accommodate the repair filament 420, 420'. In the illustrated embodiments, the width formed by the repair filament 420, 420' is approximately two diameters of the filament 420, 420' due to two portions of the filament 420, 420' being disposed in the bore 416, 416'. A person having skill in the art will understand that a location of the connecting filament 417, 417' can also be maintained by load applied by the repair filament 420, 420' and/or using one or more insertion tools, as described below.

The repair filament 420, 420' can couple to the connecting filament 417, 417' in a variety of manners. As shown, the connecting filament 417, 417' is disposed at the distal side 412d, 412d' of the anchor 412, 412' and the repair filament 420, 420' passes through and exits the axial bore 416, 416' and is coupled to the connecting filament 417, 417' by passing the repair filament 420, 420' around the connecting filament 417, 417'. The relatively small diameter of the bore 416, 416', which is barely wide enough to accommodate the repair filament 420, 420', contributes to the stability of the coupling between the repair filament 420, 420' and the connecting filament 417, 417'. For example, the system as shown in FIGS. 2A and 2B is able to remain intact due to the relative dimensions of the bore 416, 416', the repair filament 420, 420', and the connecting filament 417, 417'. Other known filament connecting techniques can also be used, including tying one or more knots to secure one filament to the other or passing one filament through the other. In some embodiments the repair filament 420, 420' may be coupled to the connecting filament 417, 417' before the device 410, 410' is packaged, while in other embodiments the repair filament 420, 420' may be coupled to the connecting filament 417, 417' by a surgeon after the device 410, 410' is removed from a package and prior to implantation.

The connecting filaments 417, 417' of FIGS. 2A and 2B can also have a variety of configurations to assist in coupling the repair filaments 420, 420' to the anchors 412, 412', respectively. Although in the illustrated embodiments the connecting filaments 417, 417' rely on an approximately folded configuration to prevent the connecting filaments 417, 417' from passing through the bores 416, 416', they can have a diameter that prevents them from passing through the bore 416, 416'. Further exemplary configurations are also described in greater detail below with respect to FIGS. 6A-13B and 16.

Anchors

Suture anchors for use in the repair devices provided herein can have a variety of configurations. The embodiments of FIGS. 1 and 2A and 2B illustrate some examples of anchors 312, 412, 412' that can be used in conjunction with the disclosures herein. In each embodiment the anchor 312, 412, 412' is generally elongate, cylindrical, and small, and is sized to fit in a pre-drilled bore formed in bone. The anchors 312, 412, 412' can include bone-engaging surface features, such as teeth, ridges, or, as shown, outer threads, to assist in securing a location of the anchors 312, 412, 412' within the pre-drilled bore, and the anchors 312, 412, 412' can each include their own bores 316, 416, 416' extending therethrough. Commercially available hard anchors, such as anchors in the Healix family and the Gryphon family from DePuy Mitek, Inc., can be used and/or modified by a person skilled in the art for use in conjunction with the disclosures herein. Further, soft anchors can also be used in conjunction with the repair filaments and connecting filaments described herein, including but not limited to soft anchors described in U.S. patent application Ser. No. 13/465,376 filed May 7, 2012, and entitled "Systems, Devices, and Methods for Securing Tissue Using Snare Assemblies and Soft Anchors," the content of which was already incorporated by reference herein in its entirety.

A size and shape of the anchor, as well as the materials from which the anchor is constructed, can depend, at least in part, on the sizes, shapes, and materials with which the anchor is used, including the sizes, shapes, and materials of the repair and connecting filaments, the obstructions through which it may pass, as well as on the type of procedure being performed. In some embodiments the anchor can have a diameter in the range of about 1 millimeter to about 12 millimeters, and in one embodiment the diameter can be about 2 millimeters, and a length in the range of about 5 millimeters to about 24 millimeters, and in one embodiment the length can be about 10 millimeters. Examples of exemplary materials that can be used to form the anchor include but are not limited to bioabsorbable elastomers, copolymer combinations such as polylactic acid-polyglycolic acid (PLA-PGA), and bioabsorbable polymers such as aliphatic polyesters, poly(amino acids), copoly(ether-esters), polyalkylenes oxalates, polyamides, tyrosine derived polycarbonates, poly(iminocarbonates), polyorthoesters, polyoxaesters, polyamidoesters, polyoxaesters containing amine groups, poly(anhydrides), polyphosphazenes, biomolecules (i.e., biopolymers such as collagen, elastin, bioabsorbable starches, etc.) and blends thereof. In some embodiments, the suture anchors can be formed from polylactic acid, or a composite blend of tricalcium phosphate and polylactic acid. The suture anchors disclosed herein can also be formed from non-absorbable materials, such as polyether ether ketone (PEEK) and polysulfone, or metals such as titanium.

Likewise, the size of the bore can depend, at least in part, on the sizes, shapes, and materials with which the anchor is used, including the sizes, shapes, and materials of the repair and connecting filaments, as well as on the type of procedure being performed. Generally, a diameter of the bore is slightly larger than a width formed by a repair filament or a connecting filament passing therethrough such that the lumen or bore is barely able to accommodate the respective filament. In some embodiments the width formed by the repair or connecting filament that passes through the lumen or bore of the anchor can be approximately the same as a diameter of the filament, while in some other embodiments, such as those illustrated in FIGS. 1 and 2A and 2B, the width formed by the repair or connecting filament that passes through the lumen or bore of the anchor can be about the size of two diameters of the filament. Such a configuration allows for the filament passing through the lumen or bore of the anchor to remain substantially associated with the anchor even when tension is not applied to the repair filament or connecting filament to keep the repair filament and connecting filament near the anchor. In some exemplary embodiments a diameter of the bore is in the range of about 0.2 millimeters to about 4 millimeters, and in one embodiment the diameter of the bore can be about 0.5 millimeters. Further, although in the illustrated embodiments the anchors include an axial bore, in some embodiments the anchor can include a transverse bore in lieu of or in addition to an axial bore. Other variations on the anchor configurations that are known to those skilled in the art can also be accommodated.

Repair Filaments

As noted above, virtually any repair filament can be used with the repair systems described herein. A person skilled in the art will be able to choose a repair filament having an appropriate size and made of an appropriate material that is suitable for use in any given procedure.

FIG. 3 illustrates one exemplary embodiment of a repair filament for use in conjunction with various anchors and connecting filaments. In the illustrated embodiment of FIG. 3 the repair filament is a snare assembly 20. As shown in FIG. 3, the snare assembly 20 can generally be flexible, can include a snare 30 formed on a first end 22, and can have a terminal end 24 opposite the first end 22, with an intermediate portion extending therebetween. The terminal end 24 can be configured to pass through an opening 32 in the snare to create a tensionable construct so the snare assembly can draw two or more objects, such as tissue and bone, closer together. Further, the snare assembly 20 can also be used as a tensioning member to help move a connecting filament against an anchor to generally secure a location of the snare assembly 20 with respect to the anchor. In some embodiments the snare assembly 20 can be used to help secure a location of an anchor within bone, for instance by applying tension to the snare assembly 20 to set the position of the anchor in bone, as known to those skilled in the art. Exemplary anchors for such embodiments include, but are not limited to, toggle-type anchors.

Optionally, a flexible sleeve 50 can be provided for encapsulating at least a portion of the snare assembly 20. As shown in FIG. 3, the sleeve encapsulates a portion of the assembly 20 starting at the terminal end 24 and extending toward the first end 22. In other embodiments the sleeve can extend more proximal than the terminal end 24. A configuration of this nature can aid a surgeon in pulling the snare assembly 20 through a portion of the body by providing extra length onto which he or she can grasp. Preferably, once the assembly 20 is implanted, the sleeve 50 can extend outside of a body as well as outside of a cannula placed in the body. This can allow the sleeve 50 to be used by a surgeon during a surgical procedure, and it can also be easily removed once it is no longer being used by the surgeon. The sleeve 50 can have a generally cylindrical configuration and can be flexible to allow it to bend as shown in various embodiments provided herein. The sleeve 50 can be useful when passing the assembly 20 through obstructions such as an anchor and/or tissue for a number of reasons. The sleeve 50 can be configured to have a smoother surface that is better configured to pass through tissue, thus reducing the possibility of fraying the filament of the snare assembly 20 or causing trauma to the tissue. Still further, because the sleeve 50 can encapsulate a plurality of filament limbs, the sleeve 50 can ease filament management by maintaining the filaments within the enclosed sleeve 50. The sleeve 50 can be removable, and thus it can be removed at any time during the procedure, or at the conclusion of the procedure.

Figure 4A:
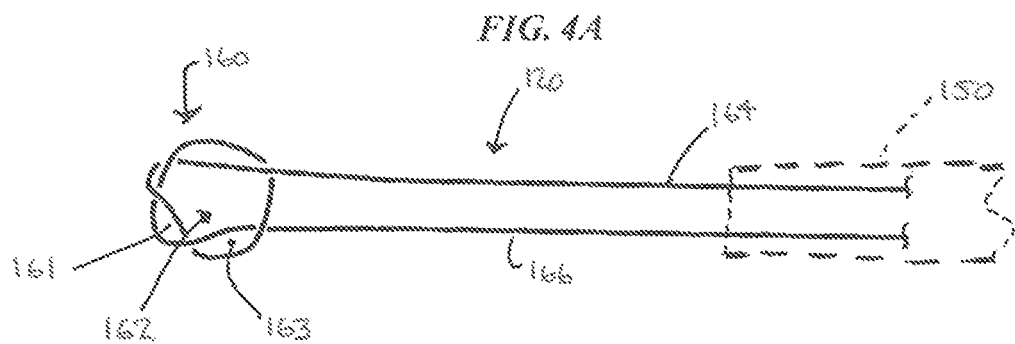
FIG. 4A is a schematic view of a snare assembly having a noose formed therein with first and second filament limbs extending to a second end.
Figure 4B:
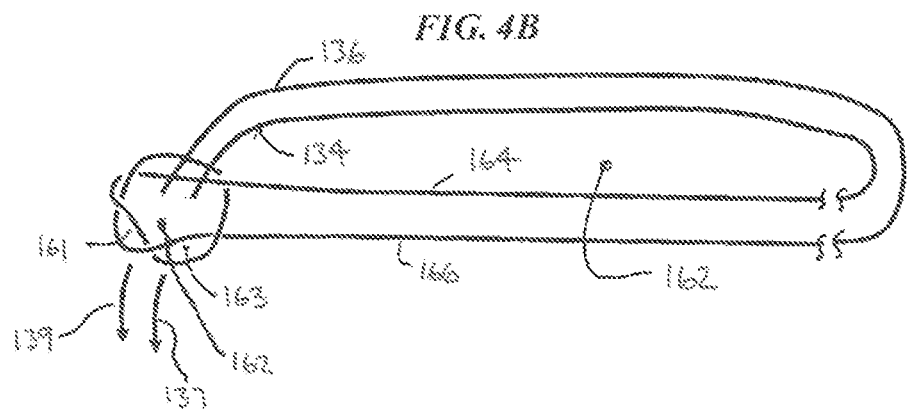
FIGS. 4B and 4C are sequential views of the snare assembly of FIG. 4A with the first and second filament limbs passed through the noose to form a snare or cinch noose.
Figure 4C:
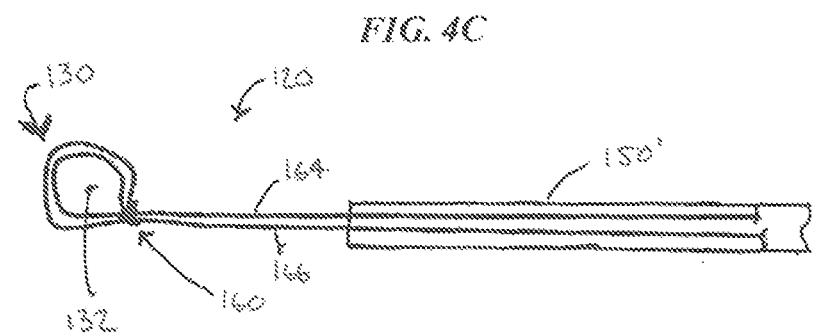

FIGS. 4A-4C illustrate one exemplary method of forming a snare assembly. As shown in FIG. 4A, the snare assembly 120 can be a filament having a noose 160 and noose limbs 164, 166. The noose 160 defines a central opening 162 and secondary openings 161 and 163 formed from a half hitch plus one additional throw of limb 166 through central opening 162. A flexible sleeve 150 is shown in phantom as it optionally encapsulates a portion of limbs 164 and 166 in certain constructions, as described in more detail below.

FIGS. 4B and 4C more particularly illustrate the formation of a cinch noose or snare 130 in an improved cinch noose construct or snare assembly 120, having an opening 132. The ends of free filament limbs 134 and 136 of the filament are passed through central opening 162, as represented by arrows 137 and 139 in FIG. 4B, which draws noose limbs 134 and 136 therethrough. Noose 160 is then tightened, as shown in FIG. 4C, to form a slidable knot for the snare 130. Alternatively, if a sleeve 150, as shown in FIG. 4A, or a sleeve 150', as shown in FIG. 4C, is not utilized, or if such sleeve is removed after being passed through tissue to be tensioned, then one or both of free limbs 134, 136 can be passed through one or both of the openings 161, 163.

Joining together at least the free filament limbs improves suture management and reduces the possibility of suture entanglement or damage by instruments, especially when passed through a cannula. For example, a surgeon or other user need only grasp and pass one sleeve 150 through the noose 160 to thereby manipulate the free filament limbs 134, 136 as a single unit.

Figure 5A:
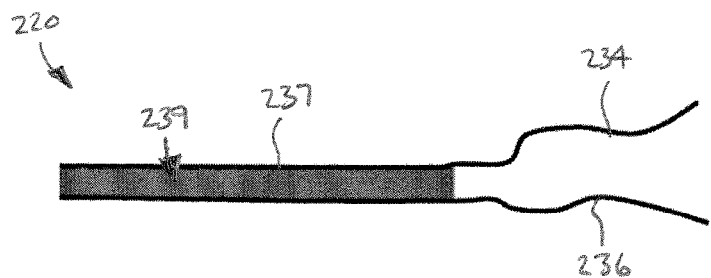
FIGS. 5A-5D are sequential views of another exemplary embodiment for forming a snare assembly having a snare at a first end and first and second filament limbs extending to a second end.
Figure 5B:
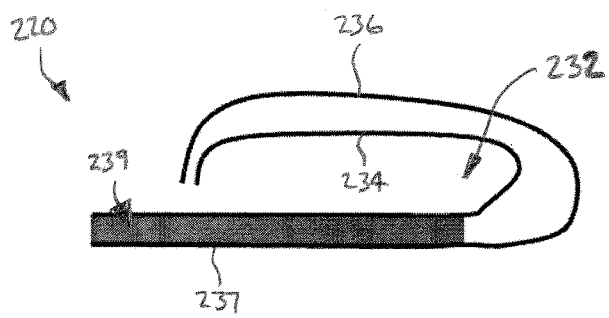
Figure 5C:
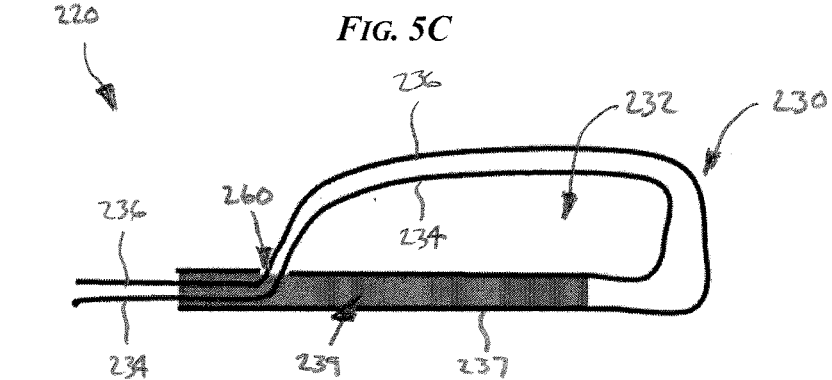
Figure 5D:
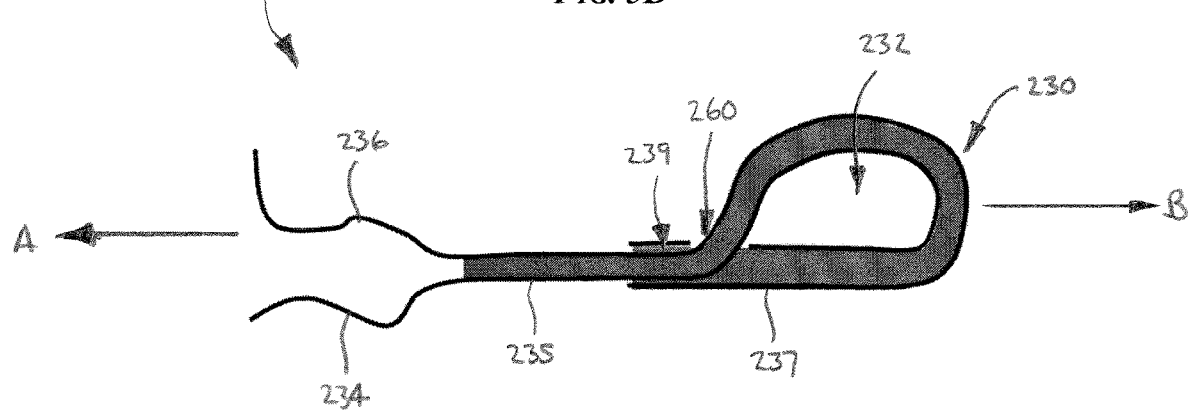

FIGS. 5A-5D illustrate another exemplary method of forming a snare assembly 220 having a snare 230 and a coaxial sliding neck 235 for use in a surgical repair construct. In this exemplary embodiment, the snare 230 is formed from a bifurcated suture filament having a tubular portion 237 with a core removed therefrom to form a cannulated portion 239 and first and second terminal limbs 234, 236. As shown in FIG. 5B, the terminal limbs 234, 236 can be curled back toward the tubular portion 237 to form a loop having an opening 232 that defines the snare 230. As shown in FIG. 5C, a bore 260 can be formed on a side of the tubular portion 237 and the terminal limbs 234, 236 can be placed into the cannulated tubular portion 239 through the bore 260. Ends of the terminal limbs 234, 236 can be fed through the cannulated portion 239, and as shown in FIG. 5D, the terminal limbs 234, 236 can be pulled distally (direction A in FIG. 5D) through the tubular portion 237 such that the tubular portion 237 is fed through itself. Accordingly, the snare 230 can be collapsed by tensioning the limbs 234, 236 and/or coaxial sliding neck 235 in approximately a first direction A, and the snare 230 can be expanded by applying a force to the snare 230 in approximately a second, opposite direction B, which pulls the limbs 234, 236 towards the snare 230. Passing the filament through itself to form a coaxial sliding neck allows the filament to have a low profile that minimizes the amount of space the construct consumes in the body and that minimizes and/or eliminates trauma associated with passing the filament through tissue.

A person skilled in the art will recognize a number of other ways that a snare for use in snare assemblies can be created and used in conjunction with the teachings herein. For example, a number of different sliding knots can be used to form snares, including but not limited to a Buntline Hitch, a Tennessee Slider, a Duncan Loop, a Hangman's Noose, and a coaxial sliding neck. To the extent the sliding knot used to form a snare affects the operation of the snare, for instance whether a limb is pulled through a knot to change the position of the knot or a knot is slid along a limb to change the position of the knot, a person skilled in the art would be able to adapt these types of knots for use with the teachings of the present invention without departing from the spirit of the present disclosure. As described herein, unless otherwise designated, a knot used to form a snare is movable away from the terminal end of the snare assembly to collapse the snare and towards the terminal end to increase a size of the snare.

The snare assemblies 20, 120, 220 can be made of any suitable flexible material, for instance a filament, including a cannulated filament, a braided filament, and a mono filament. The type, size, and strength of the flexible material can depend, at least in part, on the type of anchor with which it is used, any obstructions through which the snare assembly may pass, and the type of procedure in which it is used. In one exemplary embodiment the flexible material is an Orthocord™ filament that is commercially available from DePuy Mitek, Inc or Ethibond™ filament available from Ethicon, Inc. Generally the filament is relatively thin to minimize any trauma to tissue through which it passes. In some embodiments the filament can have a size between about a #5 filament (about 20 gauge to about 21 gauge) and about a #5-0 filament (about 35 gauge to about 38 gauge). The Orthocord™ or Ethibond™ filament can be useful because it has a braided configuration, which allows other components, including the filament itself, to pass through subcomponents of the braid without causing damage to the filament. Filaments configured to allow for a cannulated configuration, such as by removing a core therefrom or having a pre-formed cannulated configuration, can also be used. Orthocord™ suture is approximately fifty-five to sixty-five percent PDS™ polydioxanone, which is bioabsorbable, and the remaining thirty-five to forty-five percent ultra high molecular weight polyethylene, while Ethibond™ suture is primarily high strength polyester. The amount and type of bioabsorbable material, if any, utilized in the filaments of the present disclosure is primarily a matter of surgeon preference for the particular surgical procedure to be performed. Further, a length of filaments used to form the snare assemblies 20, 120, 220 can be in the range of about 15 centimeters to about 125 centimeters, and in one embodiment it can be about 60 centimeters.

A person skilled in the art will recognize that the configurations of FIGS. 3-5D are just some options for forming repair filaments such as snare assemblies. In other embodiments the repair filament can simply be a filament having proximal and distal ends and configured to slide with respect to a rigid or hard anchor, such as the repair filament 420' of FIG. 2B. In one exemplary embodiment the repair filament 420' is a #3-0 filament (about 29 gauge to about 32 gauge), such as an Orthocord™ filament that is commercially available from DePuy Mitek, Inc or Ethibond™ filament available from Ethicon, Inc. Generally the filament is relatively thin to minimize any trauma to tissue through which it passes. In some embodiments the filament can have a size between about a #5 filament (about 20 gauge to about 21 gauge) and about a #5-0 filament (about 35 gauge to about 38 gauge). Other exemplary embodiments of repair filaments that can be used in conjunction with the teachings herein are described at least in U.S. patent application Ser. No. 13/465,288 filed May 7, 2012, and entitled "Systems, Devices, and Methods for Securing Tissue," U.S. patent application Ser. No. 13/218,810 filed Aug. 26, 2011, and entitled "Surgical Filament Snare Assemblies," and U.S. patent application Ser. No. 13/465,362 filed May 7, 2012, and entitled "Systems, Devices, and Methods for Securing Tissue Using a Suture Having One or More Protrusions," the content of which are also incorporated by reference herein in their entireties.

Connecting Filaments

One or more connecting filaments can be used to assist in coupling one or more repair filaments to one or more anchors, thereby making rigid engagement members such as cross-bars or eyelets, unnecessary. FIGS. 6A-13B illustrate a variety of configurations of a connecting filament for such use. In each instance the connecting filament is coupled to the repair filament approximately at or adjacent to a distal end of the anchor and the connecting filament is configured in a manner that prevents the connecting filament from passing through an axial bore of the anchor. This configuration can generally be referred to as an altered configuration or a folded configuration. As a result, the repair filament can remain coupled to the anchor and can then be used to repair soft tissue by coupling the repair filament with the soft tissue and then using the repair filament to draw the soft tissue toward the anchor and bone in which the anchor is disposed. Further, the embodiments of FIGS. 6A-13B provide for configurations that help maintain a location of the connecting filament with respect to the anchor so that the connecting filament does not move out of place accidentally.

Figure 6A:
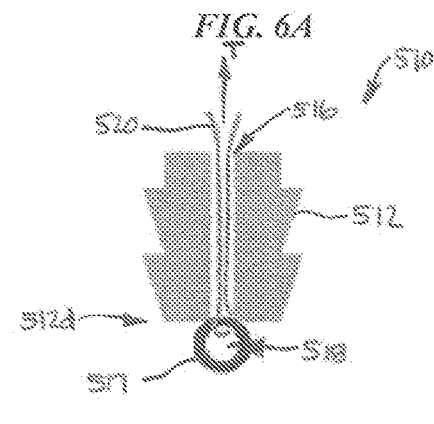
FIG. 6A is a schematic view of one exemplary embodiment of a surgical soft tissue repair device that includes an anchor, a repair filament, and one exemplary embodiment of a connecting filament configuration for coupling the repair filament to the anchor.
Figure 6B:
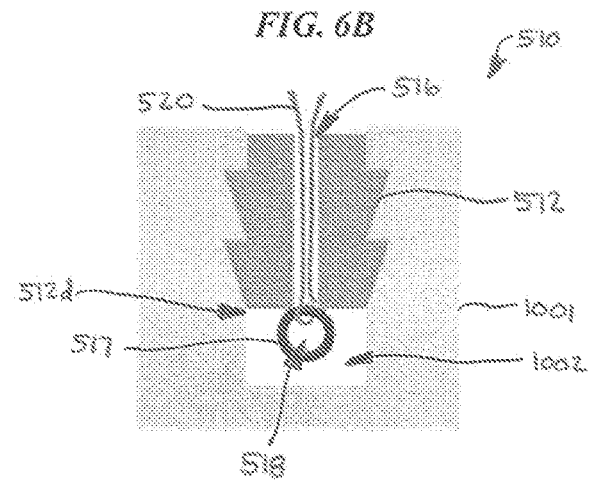
FIG. 6B is a schematic view of the surgical soft tissue repair device of FIG. 6A disposed in bone.

FIGS. 6A and 6B illustrate one exemplary embodiment of a surgical soft tissue repair device 510 that includes a hard anchor 512 having an axial bore 516 formed therethrough, a repair filament 520, and a connecting filament 517. As shown, the connecting filament 517 can be a continuous loop and the repair filament 520 can pass through a center 518 of the continuous loop approximately at or adjacent to a distal end 512d of the anchor 512. The diameter of the connecting filament 517 can be large enough such that even when the continuous loop is flexible and is compressed so that a left side of the loop contacts a right side of the loop, the resulting folded width of the connecting filament 517 can still be larger than the diameter of the axial bore 516 so that the connecting filament 517 does not pass through the bore 516 when tension is applied to the repair filament 520 approximately in a direction T, which can occur during and after a surgical procedure. As shown in FIG. 6B, the device 510 can be implanted in a bore 1002 formed in bone 1001. Because a diameter of the bore 516 is generally the same size as or only slightly larger than a width formed by the repair filament 520, the repair filament 520 does not generally fall out of the bore 516. The repair suture can also be kept in place by an insertion tool assembly, as discussed in greater detail below. Further, as illustrated in FIG. 6B, because there is generally a relatively small distance between the distal end 512d of the anchor 512 and the bottom of the bore 1002 into which the anchor 512 is inserted, e.g., in the range of about 1 millimeter to about 15 millimeters, the repair filament 520 can remain near the anchor 512 for use in a procedure even if the repair filament 520 were to fall distally away from the anchor 512.

Figure 7A:
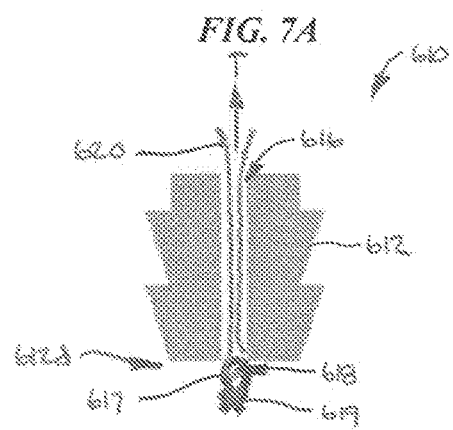
FIG. 7A is a schematic view of another exemplary embodiment of a surgical soft tissue repair device that includes an anchor, a repair filament, and another exemplary embodiment of a connecting filament configuration for coupling the repair filament to the anchor.
Figure 7B:
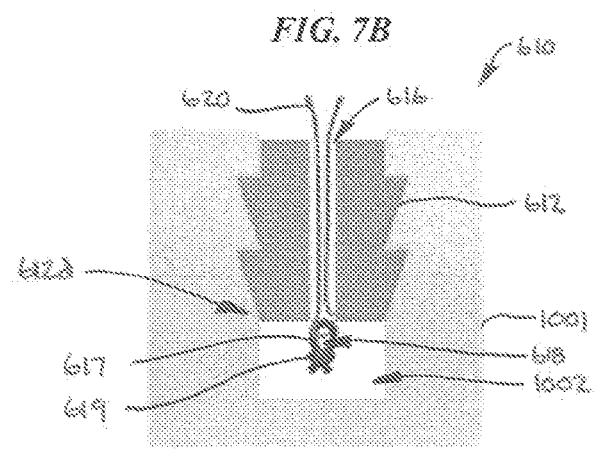
FIG. 7B is a schematic view of the surgical soft tissue repair device of FIG. 7A disposed in bone.

FIGS. 7A and 7B illustrate another exemplary embodiment of a surgical soft tissue repair device 610 that includes a hard anchor 612 having an axial bore 616 formed therethrough, a repair filament 620, and a connecting filament 617. As shown, the connecting filament 617 can be a knotted construction forming a continuous loop and the repair filament 620 can pass through a loop 618 formed by the knotted construction approximately at or adjacent to a distal end 612d of the anchor 612. One or more knots 619 can be formed in the connecting filament 617 using techniques known to those skilled in the art, including techniques described in other patent applications incorporated by reference herein. The knots 619 can be pre-formed so that a surgeon does not need to tie the knots during a surgical procedure, although a surgeon can choose to tie one or more knots 619 on site. The resulting configuration from the knotted construction can result in the connecting filament 617 having a folded width that is greater than the diameter of the axial bore 616 even when compressed so that the connecting filament 617 does not pass through the bore 616 when tension is applied to the repair filament 620 approximately in a direction T. As shown in FIG. 7B, the device 610 can be implanted in a bore 1002 formed in bone 1001, and the depth of the bore 1002 can be such that a distance between the distal end 612d of the anchor 612 and the bottom of the bore 1002 is relatively small, in the range of about 1 millimeter to about 15 millimeters.

Figure 8A:
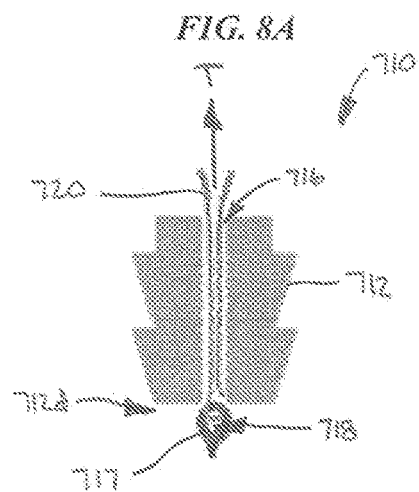
FIG. 8A is a schematic view of still another exemplary embodiment of a surgical soft tissue repair device that includes an anchor, a repair filament, and still another exemplary embodiment of a connecting filament configuration for coupling the repair filament to the anchor.
Figure 8B:
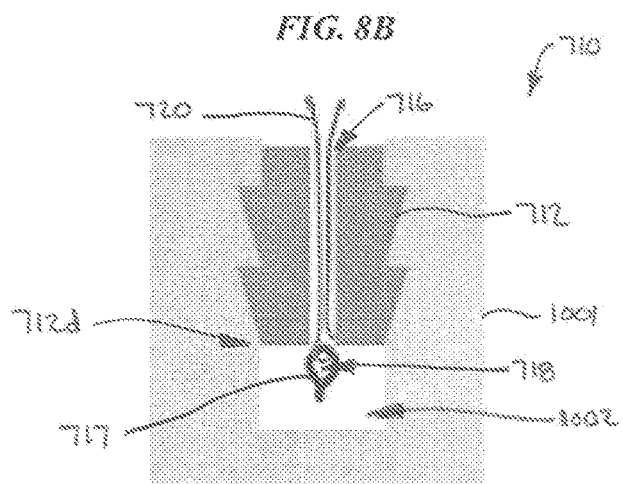
FIG. 8B is a schematic view of the surgical soft tissue repair device of FIG. 8A disposed in bone.

FIGS. 8A and 8B illustrate still another exemplary embodiment of a surgical soft tissue repair device 710 that includes a hard anchor 712 having an axial bore 716 formed therethrough, a repair filament 720, and a connecting filament 717. As shown, portions of the connecting filament 717 are glued together to form a loop and the repair filament 720 can pass through a center 718 of the loop approximately at or adjacent to a distal end 712d of the anchor 712. The resulting loop can be sized such that in this folded configuration it cannot pass through the axial bore 716. As shown, the diameter of the loop is greater than the diameter of the axial bore 716. Further, because the connecting filament 717 can be flexible, even when the continuous loop is compressed such that a left side of the loop contacts the right side of the loop, the resulting folded width of the connecting filament 717 can still be larger than the diameter of the axial bore 716 so that the connecting filament 717 does not pass through the bore 716 when tension is applied to the repair filament 720 approximately in a direction T. In one embodiment a width of the strand of filament in an unfolded configuration used to form the glued loop is less than a diameter of the bore 716. This allows the strand in the unfolded configuration to be passed through the bore 716 from a proximal end of the bore 716 to a distal end of the bore 716 when first constructing the device 710 and then subsequently glued to form the loop, i.e., the folded configuration, thereby preventing the strand from being passed back through the bore 716 when tension is applied to the repair filament 720 approximately in the direction T. As shown in FIG. 8B, the device 710 can be implanted in a bore 1002 formed in bone 1001, and the depth of the bore 1002 can be such that a distance between the distal end 712d of the anchor 712 and the bottom of the bore 1002 is relatively small, in the range of about 1 millimeter to about 15 millimeters.

Figure 9A:
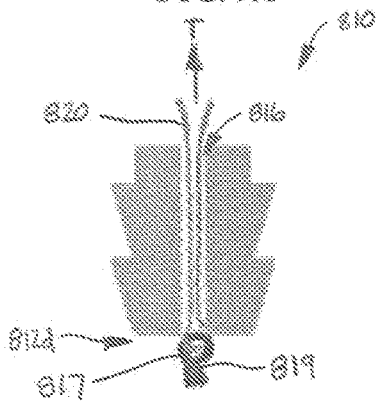
FIG. 9A is a schematic view of yet another exemplary embodiment of a surgical soft tissue repair device that includes an anchor, a repair filament, and yet another exemplary embodiment of a connecting filament configuration for coupling the repair filament to the anchor.
Figure 9B:
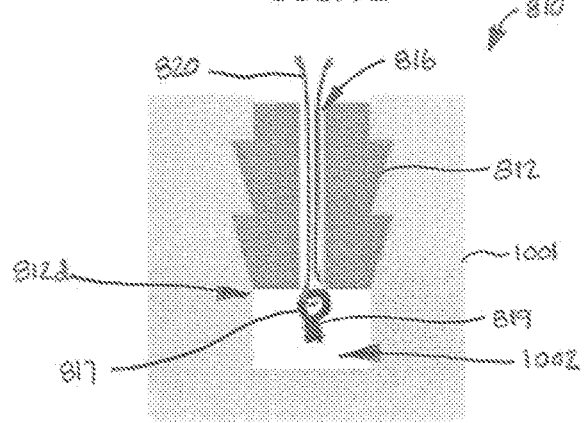
FIG. 9B is a schematic view of the surgical soft tissue repair device of FIG. 9A disposed in bone.

FIGS. 9A and 9B illustrate yet another exemplary embodiment of a surgical soft tissue repair device 810 that includes a hard anchor 812 having an axial bore 816 formed therethrough, a repair filament 820, and a connecting filament 817. As shown, the connecting filament 817 pierces through itself multiple times to form a continuous loop, i.e., a folded configuration, and the repair filament 820 can pass through a center of the loop approximately at or adjacent to a distal end 812d of the anchor 812. The resulting configuration can result in the connecting filament 817 having a folded width that is greater than the diameter of the axial bore 816 even when compressed so that the connecting filament 817 does not pass through the bore 816 when tension is applied to the repair filament 820 approximately in a direction T. As shown in FIG. 9B, the device 810 can be implanted in a bore 1002 formed in bone 1001, and the depth of the bore 1002 can be such that a distance between the distal end 812d of the anchor 812 and the bottom of the bore 1002 is relatively small, in the range of about 1 millimeter to about 15 millimeters.

Figure 10A:
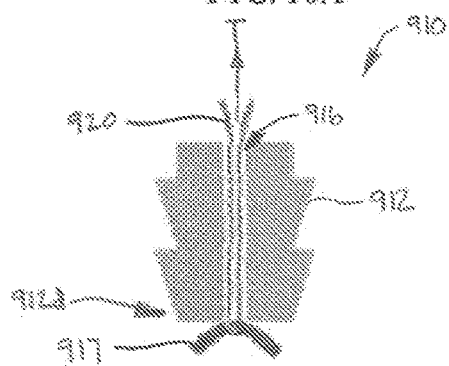
FIG. 10A is a schematic view of another exemplary embodiment of a surgical soft tissue repair device that includes an anchor, a repair filament, and another exemplary embodiment of a connecting filament configuration for coupling the repair filament to the anchor.
Figure 10B:
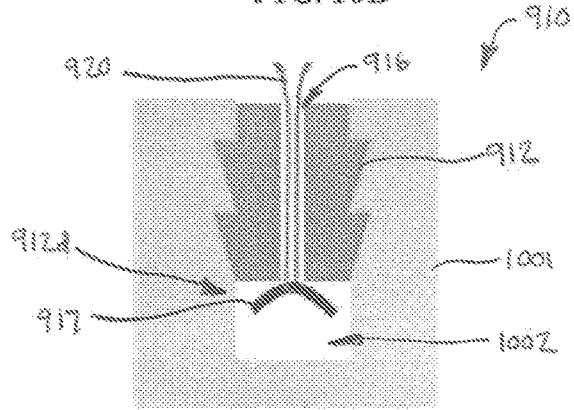
FIG. 10B is a schematic view of the surgical soft tissue repair device of FIG. 10A disposed in bone.

FIGS. 10A and 10B illustrate another exemplary embodiment of a surgical soft tissue repair device 910 that includes a hard anchor 912 having an axial bore 916 formed therethrough, a repair filament 920, and a connecting filament 917. As shown, the connecting filament 917 is of a nature similar to the connecting filament described above with respect to FIGS. 2A and 2B except rather than having the repair filament 920 disposed around the connecting filament 917 the repair filament 920 is disposed through the connecting filament 917 approximately at or adjacent to a distal end 912d of the anchor 912. A width formed by two portions of the connecting filament 917 being compressed together is such that the folded width is greater than the diameter of the axial bore 916 so that the connecting filament 917 does not pass through the bore 916 when tension is applied to the repair filament 920 approximately in a direction T. Further, in some embodiments a width of the connecting filament 917 in an uncompressed and unfolded state can be less than a diameter of the bore 916 such that the connecting filament 917 can be moved to the distal end 912d of the anchor 912 by passing the connecting filament 917 distally through the bore 916, for instance when first constructing the device 910. As shown in FIG. 10B, the device 910 can be implanted in a bore 1002 formed in bone 1001, and the depth of the bore 1002 can be such that a distance between the distal end 912d of the anchor 912 and the bottom of the bore 1002 is relatively small, in the range of about 1 millimeter to about 15 millimeters.

Figure 11A:
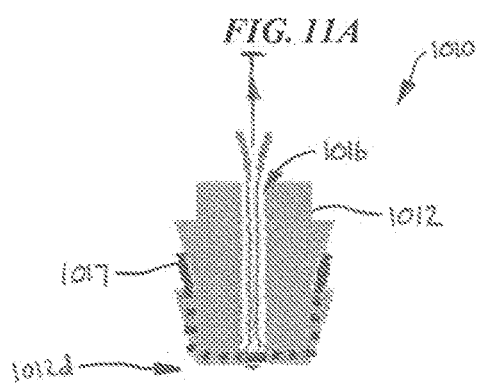
FIG. 11A is a schematic view of still another exemplary embodiment of a surgical soft tissue repair device that includes an anchor, a repair filament, and still another exemplary embodiment of a connecting filament configuration for coupling the repair filament to the anchor.
Figure 11B:
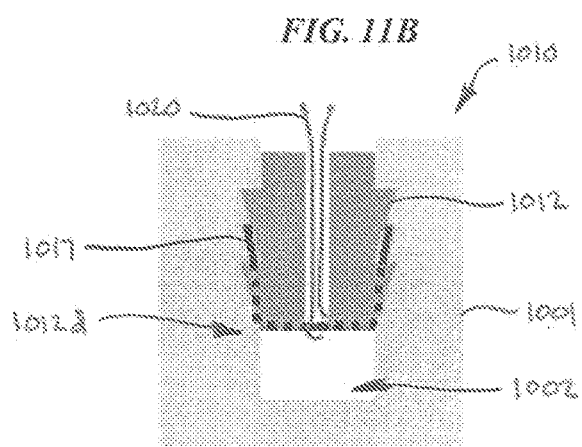
FIG. 11B is a schematic view of the surgical soft tissue repair device of FIG. 11A disposed in bone.

FIGS. 11A and 11B illustrate still another exemplary embodiment of a surgical soft tissue repair device 1010 that includes a hard anchor 1012 having an axial bore 1016 formed therethrough, a repair filament 1020, and a connecting filament 1017. As shown, the connecting filament 1017 is disposed within a distal side 1012d of the anchor 1012. By way of non-limiting example, the anchor 1012 can include bores or other structures for receiving ends of the connecting filament 1017 to maintain a general location of the connecting filament 1017, which in turn can maintain a general location of the repair filament 1020 with respect to the anchor 1012 due to the repair filament 1020 being coupled to the connecting filament 1017. The configuration of the device 1010 in general can be such that the attachment of the connecting filament 1017 to the anchor 1012 by way of bores or other structures for receiving ends of the connecting filament 1017 does not carry the load resulting from tissue attachment. In the illustrated embodiment the repair filament 1020 is passed around the connecting filament 1017, but in other embodiments the repair filament 1020 can pass through the connecting filament 1017. Because the connecting filament 1017 is generally held in place at the distal side 1012d of the anchor 1012, the connecting filament 1017 does not pass through the bore 1016 when tension is applied to the repair filament 1020 approximately in a direction T. As shown in FIG. 11B, the device can be implanted in a bore 1002 formed in bone 1001. While in some instances the connecting filament 1017 can be secured to the anchor 1012 prior to implantation, in other instances the fit of the anchor 1012 in the bore 1002 can generally maintain the location of the connecting filament 1017 with respect to the anchor 1012 to prevent the connecting filament 1017, and thus the repair filament 1020, from falling away from the anchor 1012.

FIGS. 12A and 12B illustrate yet another exemplary embodiment of a surgical soft tissue repair device 1110 that includes a hard anchor 1112 having an axial bore 1116 formed therethrough, a repair filament 1120, and a connecting filament 1117. As shown, the connecting filament 1117 is located approximately at a distal end 1112d of the anchor 1112 with the repair filament 1120 being looped around it. In other embodiments the repair filament 1120 can pass through the connecting filament 1117. The location of the connecting filament 1117 with respect to the anchor 1112 can be maintained, for example, by a guide (not illustrated) disposed around the anchor 1112, as described in greater detail below with respect to FIGS. 17-19E. Because the connecting filament 1117 is generally held in place at the distal side 1112d of the anchor 1112, the connecting filament 1117 does not pass through the bore 1116 when tension is applied to the repair filament 1120 approximately in a direction T. As shown in FIG. 12B, the device can be implanted in a bore 1002 formed in bone 1001. As illustrated the connecting filament 1117 can become impinged between the anchor 1112 and walls of the bore 1002 to generally maintain the location of the connecting filament 1117 with respect to the anchor 1112 to prevent the connecting filament 1117, and thus the repair filament 1120, from falling away from the anchor 1112. In some embodiments the connecting filament 1117 can generally conform to the shape of the anchor 1112, as shown.

Although FIGS. 6-12B illustrate the engagement between the respective repair filaments and connecting filaments to be approximately at or distal to the distal ends of the respective anchors, it is understood that tension applied to the repair filaments can cause the location of the engagement between the repair filaments and the connecting filaments to shift proximally to a position slightly adjacent to the distal ends of the respective anchors.

FIGS. 13A and 13B illustrate another exemplary embodiment of a surgical soft tissue repair device 1210 that includes a hard anchor 1212 having an axial bore 1216 formed therethrough, a repair filament 1220, and a connecting filament 1217. The axial bore 1216 can be stepped such that a distal end 1216*d* of the bore 1216 has a diameter that is greater than a remaining portion of the bore 1216. As shown, the connecting filament 1217 is of a nature similar to the filaments 417, 417', and 917 described above with respect to FIGS. 6A, 6B, 10A, and 10B, and in the illustrated embodiment the repair filament 1220 is disposed around the connecting filament 1217 approximately at or adjacent to a distal end 1212*d* of the anchor 1212. Similar to FIGS. 6-12B, tension applied to the repair filament 1220 can cause the location of the engagement between the repair filament 1220 and the connecting filament 1217 to shift slightly proximally. A width of the connecting filament 1217 when two portions thereof are compressed together is such that the connecting filament 1217 can be disposed within the stepped portion at the distal end 1216*d* of the bore, but it is greater than the diameter of the remaining portion of the axial bore 1216 so that the connecting filament 1217 does not pass through the bore 1216 when tension is applied to the repair filament 1220 approximately in a direction T. As shown in FIG. 13B, the device 1210 can be implanted in a bore 1002 formed in bone 1001, and the depth of the bore 1002 can be such that a distance between the distal end 1212*d* of the anchor 1212 and the bottom of the bore 1002 is relatively small, in the range of about 1 millimeter to about 15 millimeters.

A person skilled in the art will recognize that the connecting filament configurations described herein for maintaining a location of repair filament with respect to an anchor are only a sample of a wide variety of configurations that can be used to achieve the same results. The connecting filament can have any number of shapes and configurations that assist in maintaining a location of the repair filament with respect to an anchor for use in soft tissue repair without departing from the spirit of the present disclosure. Likewise, the connecting filament can be formed using a variety of filament types, including but not limited to a cannulated filament, a braided filament, and a mono filament. The type, size, and strength of the filament can depend, at least in part, on the other materials of the anchor and repair filament, the obstructions through which it may pass, the type of configuration planned for the connecting filament, and the type of procedure in which the connecting filament is used. Generally, the connecting filament has a diameter that is larger than the diameter of the repair filament. Further, the diameter of the connecting filament is such that in certain configurations, such as altered, folded configurations, it is unable to pass through a bore of an anchor, for instance because the width formed by the connecting filament is larger than the diameter of the bore of the anchor. In one exemplary embodiment the connecting filament is formed from a #2 filament (about 23 gauge to about 24 gauge), such as an Orthocord™ filament that is commercially available from DePuy Mitek, Inc. or Ethibond™ filament available from Ethicon Inc. In some embodiments the connecting filament can have a size between about a #4 filament (about 21 gauge to about 22 gauge) and about a #4-0 filament (about 32 gauge to about 34 gauge). A length of the connecting filament can be in the range of about 2 millimeters to about 25 millimeters, and in one embodiment the length is about 10 millimeters.

While the present disclosure provides a number of different constructions and configurations for surgical soft tissue repair devices, including various configurations of repair filaments, connecting filaments, and anchors, a person skilled in the art will recognize a variety of other constructions the device, the anchor, the repair filament, and the connecting filament can have without departing from the spirit of the present disclosure.

Use of Soft Tissue Repair Devices

FIGS. 14A-14G illustrate one exemplary method for performing a tissue repair using the repair construct illustrated in FIG. 1. A surgical opening can be formed through skin 1000 and a cannula can be passed therethrough to access a surgical repair site according to well known techniques. Although cannulas are often used to define a channel through which the procedure can be performed, the cannula is not shown in FIGS. 14A-14G for clarity of illustration. Accordingly, to the extent the figures show components of the systems and devices passing through skin 1000, these components would typically extend through the cannula, which itself is passed through the skin 1000. Further, although the devices and methods described herein are particularly useful for minimally invasive surgery, such as arthroscopic surgery, they can also be used in open surgical procedures. After a surgical opening is formed through skin 1000, a bore 1002 for inserting the device 310 can be formed in bone 1001 at the surgical repair site using techniques known to those having skill in the art.

As shown in FIG. 14A, the connecting filament 317 can be distal of the snare assembly 320 (or other connecting filament), and more particularly can be placed in the axial bore 316 with its distal end 317*d* in the distal end 316*d* of the bore 316. The anchor 312 can be fixated into the bore 1002 using ordinary techniques, such as with a driver that screws or taps the anchor 312 into place. The snare assembly 320 and the connecting filament 317 can be coupled before, during, or after fixation of the anchor 312 into the bore 1002, and in one exemplary embodiment the snare assembly 320 is looped through the connecting filament 317 prior to inserting the anchor 312 into the bore 1002. In the illustrated embodiment the connecting filament 317 is not fixedly coupled to the anchor 312, but because a diameter of the bore 316 is barely larger than a width formed by the loop of the connecting filament 317, generally the connecting filament 317 can remain disposed within the bore 316. The distal end 317*d* of the connecting filament 317 can then be brought into an anchored configuration in which it engages the distal end 316*d* of the bore 316 by applying tension to the repair filament 320 approximately in a direction T. The tension can be applied by the surgeon during the procedure and by the tissue during and after the procedure is completed. In the anchored configuration, the connecting filament 317 couples the repair filament 320 to the anchor 312. In alternative embodiments, the anchor 312 can include one or more coupling features for receiving the connecting filament 317 to maintain a location of the connecting filament 317 with respect to the anchor 312.

As shown in FIG. 14B, the terminal end 324 of the repair filament 320 can be passed into and through at least a portion of tissue 1003 detached from the bone 1001. Optionally, a needle or similar tool or device can be coupled to the terminal end 324 to assist with threading the repair filament 320 through the tissue 1003. Likewise, other shuttling techniques known to a person skilled in the art can also be used to pass the snare assembly 320 through the tissue.

Figure 14C:
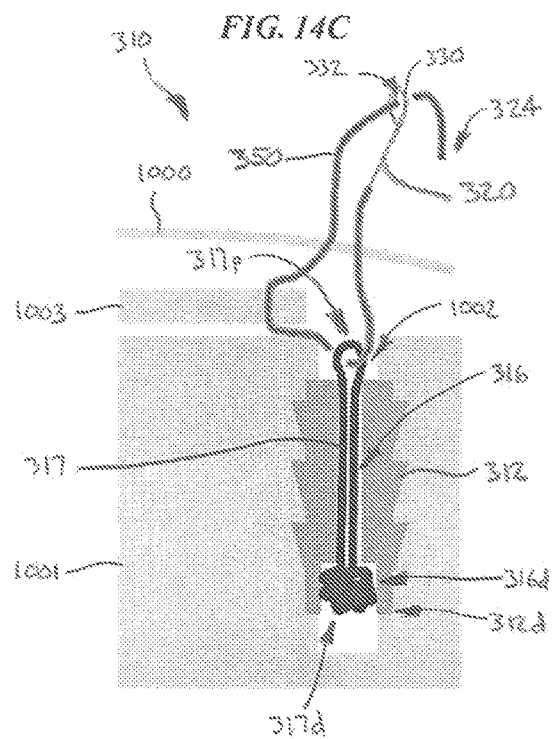
Figure 14D:
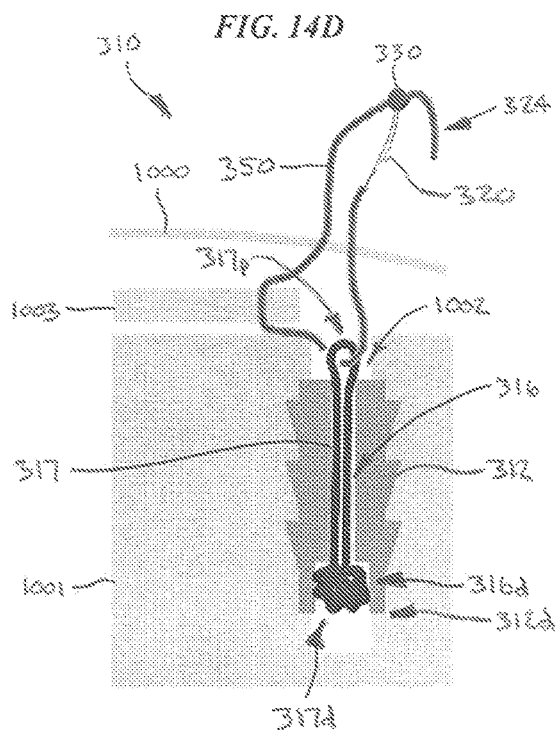

As shown in FIGS. 14C and 14D, a portion of the terminal end 324 can be passed through the opening 332 of the snare 330 and the snare 330 can be collapsed or dressed in a manner consistent with its snare type. Thus, in the illustrated embodiment the snare 330 can be collapsed by moving the knot that forms the snare 330 away from the terminal end 324.

Figure 14E:
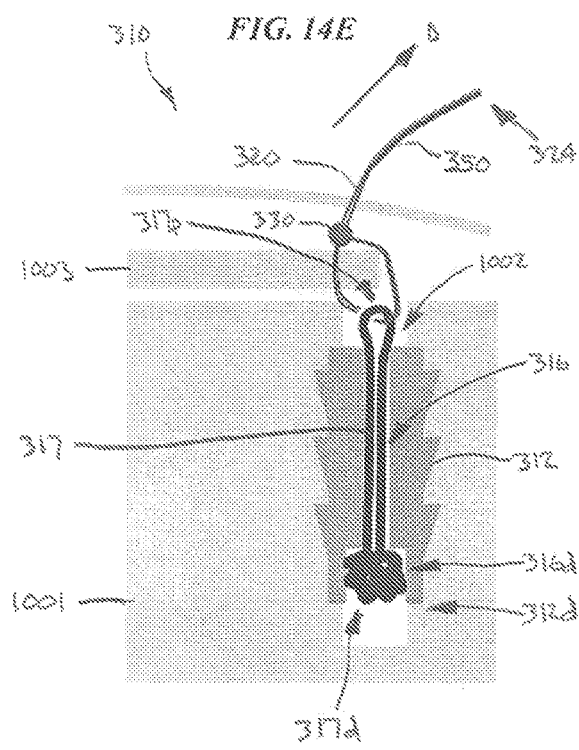
Figure 14F:
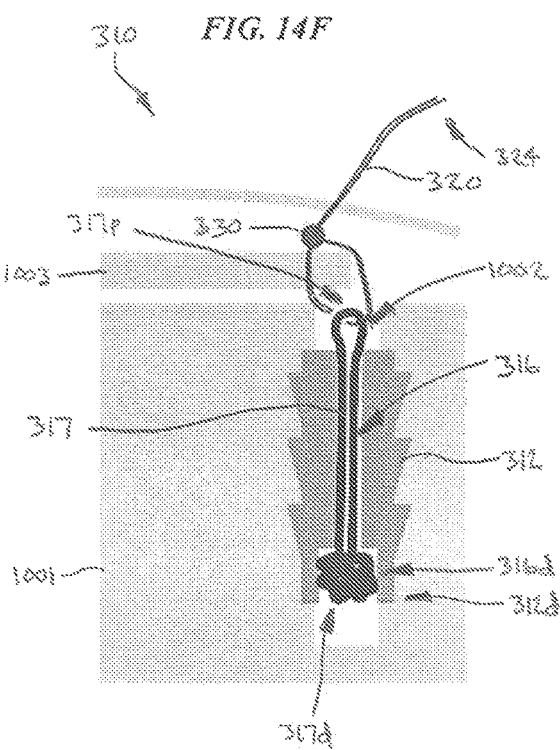
Figure 15C:
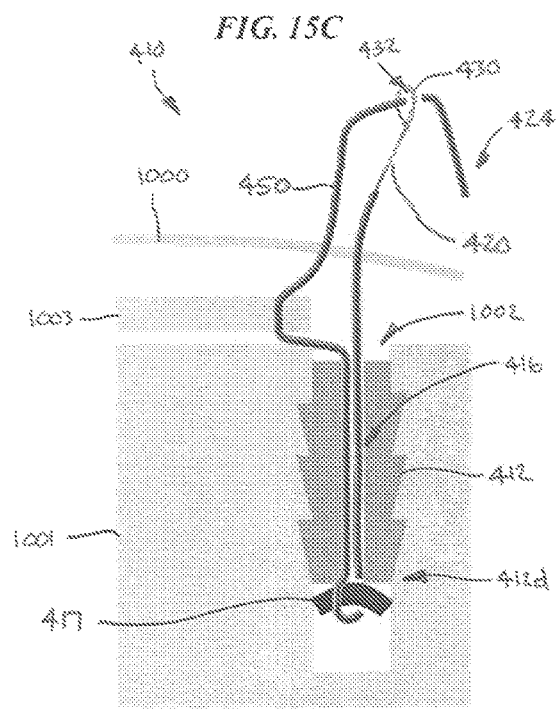
Figure 15D:
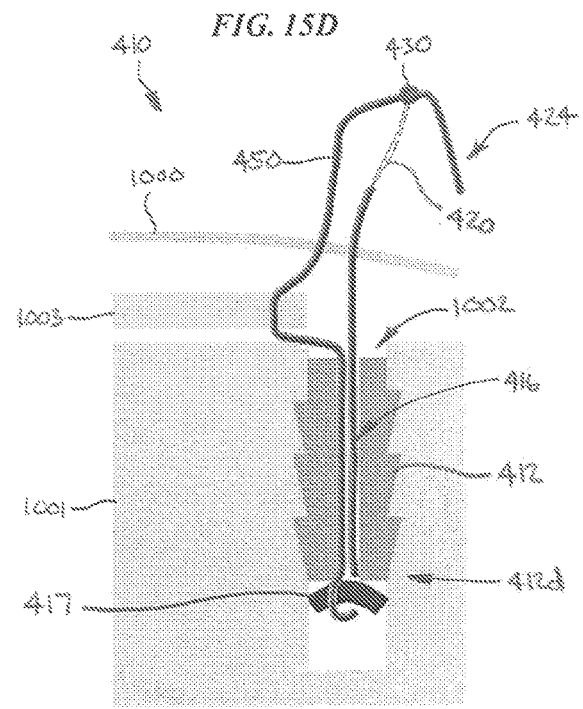
Figure 15E:
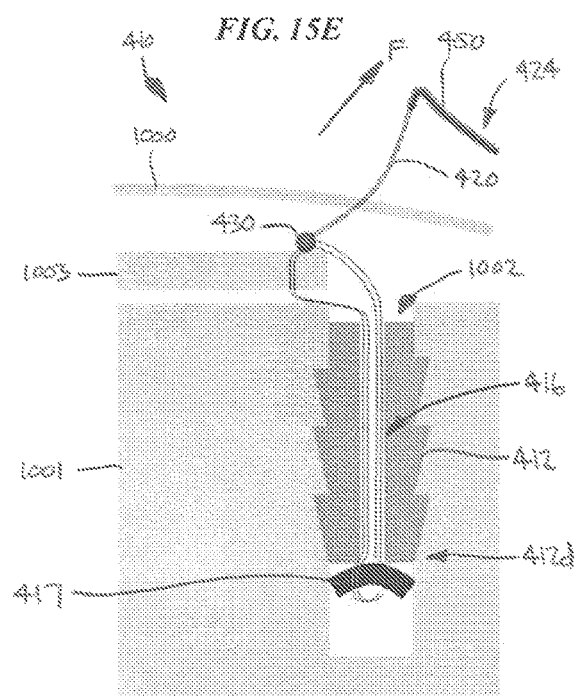
Figure 15F:
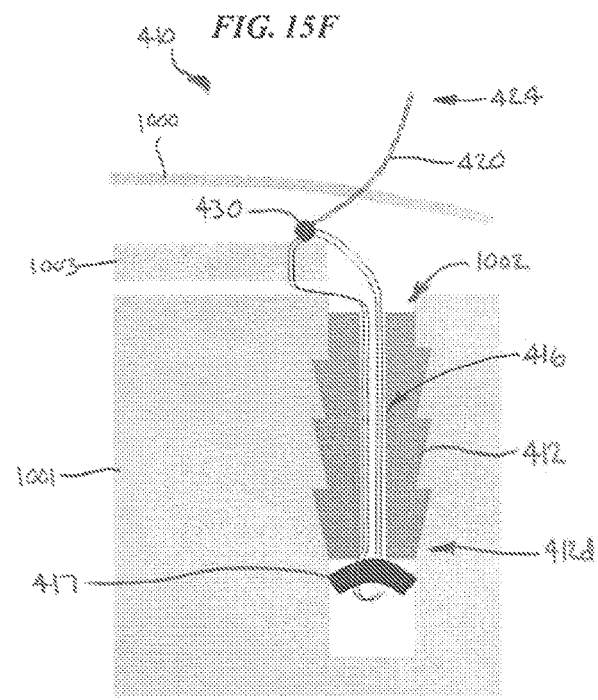
Figure 15G:
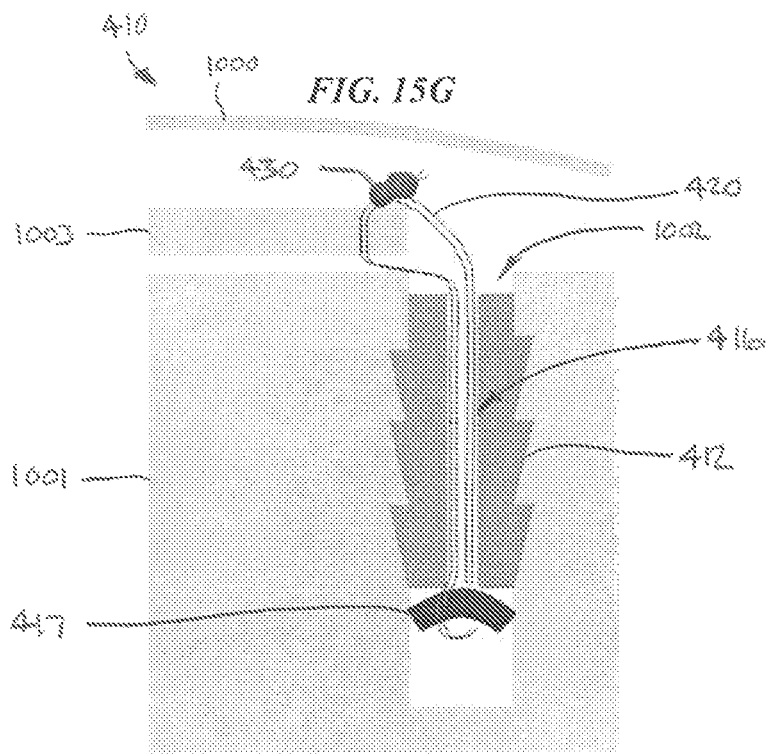
Figure 16:
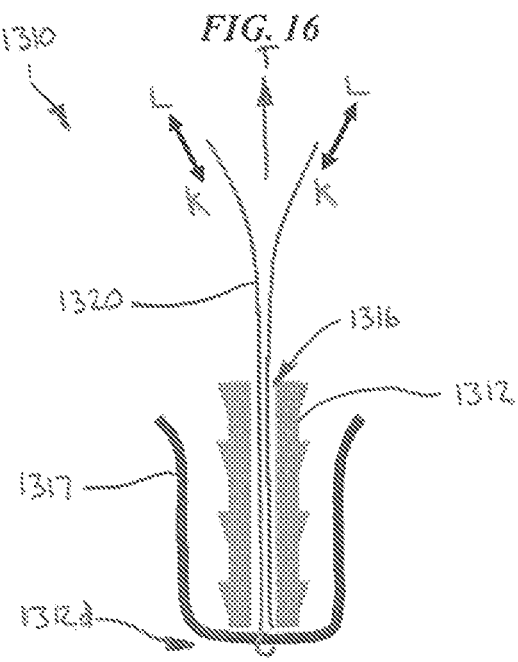
FIG. 16 is a schematic view of still another exemplary embodiment of a surgical soft tissue repair device.

As shown in FIG. 14E, tension can be applied to the terminal end 324 by pulling approximately in a direction D, thereby causing the collapsed snare 330 to slide distally toward the tissue 1003 in a zip line-like manner until the snare 330 is adjacent to the tissue 1003. This, in turn, can cause the tissue 1003 to move toward and into contact with the bone 1001. Alternatively, tension can be applied to the terminal end 324 before the snare 330 is dressed and after the snare 330 is adjacent to the tissue 1003, or some combination of the two actions can be used, such as partially dressing the snare 330 before zip-lining it toward the tissue 1003. As shown in FIG. 14E, in embodiments that include the sleeve 350, as the snare 330 is slid distally toward the tissue 1003, the sleeve 350 can move proximally, out of the body. The sleeve 350, if included, can be removed at any time, as shown in FIG. 14F for example. Final tensioning can be carried out by applying tension to the terminal end 324, or the sleeve 350 if it remains associated with the snare assembly.

As shown in FIG. 14G, one or more half-hitches can be formed proximate to the collapsed snare to allow for incremental or ratchet-like tensioning and/or to maintain a location of the collapsed snare. After a first half-hitch is formed, the repair filament 320 can be further tensioned in an incremental or ratchet-like manner by applying tension to the repair filament 320. The addition of a second or more half-hitches can lock the location of the collapsed snare. Excess filament can then be trimmed and removed to complete the procedure. Other techniques known to those skilled in the art can be used to maintain the location of the collapsed snare, and thus the approximated tissue.

FIGS. 15A-15G illustrate one exemplary method for performing a tissue repair using the repair construct illustrated in FIG. 2A. A surgical opening can be formed through skin 1000 and a cannula can be passed therethrough to create a surgical repair site according to well known techniques. Similar to FIGS. 14A-14G, although cannulas are often used to define a channel through which the procedure can be preformed, the cannula is not shown in FIGS. 15A-15G for clarity of illustration. Accordingly, to the extent the figures show components of the systems and devices passing through skin 1000, these components would typically be extending through the cannula, which itself is passed through the skin 1000. After a surgical opening is formed through skin 1000, a bore 1002 for inserting the device 410 can be formed in bone 1001 at the surgical repair site using techniques known to those having skill in the art.

In the illustrated embodiment of FIG. 15A, the repair filament 420 is not fixedly coupled to the anchor 412, but because a diameter of the bore 416 is barely larger than a width formed by the two portions of the repair filament 420 disposed therein, generally the repair filament 420 can remain disposed within the bore 416. Alternatively, the repair filament 420 can be held in place by an insertion tool. Further, the connecting filament 417 can be brought into an anchored configuration in which the connecting filament 417 engages but does not pass through the bore 416 on the distal side 412d of the anchor 412 by applying tension to the repair filament 420 approximately in a direction T. The tension can be applied by the surgeon during the procedure and by the tissue during and after the procedure is completed. In the anchored configuration, the connecting filament 417 couples the repair filament 412 to the anchor 420 approximately at or adjacent to the distal end 412d of the anchor 412. In alternative embodiments, the anchor 412 can include one or more coupling features for receiving the connecting filament 417 to maintain a location of the connecting filament 417 with respect to the anchor 412.

Once the device 410 is disposed in the bore 1002, it can then be operated in a manner similar to as described with respect to FIGS. 14B-14G. Thus, at least a portion of the terminal end 424 of the repair filament 420 can be passed through at least a portion of the tissue 1003 and through the opening 432 in the snare 430 and the snare 430 can be collapsed or dressed, for instance by moving the knot that forms the snare 430 away from the terminal end 424. The snare 430 can be slid distally toward the tissue 1003 by applying tension to the terminal end 424 approximately in a direction F, which can result in the snare 430 being adjacent to the tissue 1003 and the tissue 1003 moving towards the bone 1001. Final tensioning and removal of the sleeve 450, if used, can occur, and one or more half-hitches can be formed proximate to the collapsed snare 430 to allow for incremental or ratchet-like tensioning and/or to maintain a location thereof. Excess filament can then be trimmed and removed to complete the procedure.

Procedures that use the devices and systems described herein can withstand both high levels of load that result from tissue and bone movement after the procedure is completed and high levels of load that can occur while the procedure is being performed. For example, procedures that use devices such as the devices 310 and 410 can withstand levels of load approximately in the range of about 2 kilograms and about 50 kilograms, and in one embodiment can withstand levels of load of about 15 kilograms.

Insertion Assembly and Use Thereof

FIGS. 16-19E illustrate one exemplary way by which a surgical soft tissue repair device can be implanted in bone. The surgical soft tissue repair device 1310 illustrated in FIG. 16 has a construction similar to the device 1110 described with respect to FIGS. 12A and 12B in that it includes a hard anchor 1312 having an axial bore 1316 formed therethrough, a repair filament 1320, and a connecting filament 1317, with the connecting filament 1317 being located at a distal side 1312d of the anchor 1312 and the repair filament 1320 being disposed around the connecting filament 1317. A diameter of the axial bore 1316 can be barely larger than a width formed by the two portions of the repair filament 1320 disposed in the bore 1316, and the repair filament 1320 can be slidably coupled to the connecting filament 1317 such that it can move distally approximately in a direction K and proximally approximately in a direction L as illustrated by the arrows in FIG. 16 without falling away from the anchor 1312. Alternatively, the repair filament 420 can be held in place by an insertion tool. In other embodiments the repair filament 1320 can pass through the connecting filament 1317. The location of the connecting filament 1317 with respect to the anchor 1312 can be maintained, for example, by a guide (not illustrated) disposed around the anchor, as described in greater detail below with respect to FIGS. 17-19E.

The device 1310 can be removably coupled to an insertion tool 1370 configured to assist in placing the anchor 1312 in bone. As shown in FIG. 17, the insertion tool 1370 can be in the form of an elongate tube that includes a proximal end 1370p having a handle 1372, a distal end 1370d configured to mate with the anchor 1312, and a bore 1376 extending through the insertion tool 1370 to allow the repair filament 1320 to extend therethrough. The handle 1372 can be manipulated by a surgeon to move the insertion tool 1370, and thus the anchor 1312 coupled thereto, in both a proximal direction and a distal direction. While a number of different configurations can be used to couple the anchor 1312 to the insertion tool 1370, in the illustrated embodiment tension is applied to the repair filament 1320 approximately in a direction T by tucking a proximal portion 1320*p* of the repair filament 1320 into a receiving feature of the handle 1372. A proximal end 1312*p* of the anchor 1312 thus abuts the distal end 1370*d* of the insertion tool 1370, rendering the anchor 1312 removably coupled to the insertion tool 1370. In alternative configurations, any number of removable mating techniques and/or configurations can be used to allow the anchor 1312 to be removably coupled to the insertion tool 1370. By way of non-limiting example, the proximal end 1312*p* of the anchor 1312 can be removably coupled to the distal end 1370*d* of the insertion tool 1370 by a male-female coupling feature that can be easily connected and disconnected by a surgeon from the proximal end 1370*p* of the insertion tool 1370.

The insertion tool 1370 can have a variety of shapes and configurations, as can the components thereof, depending at least in part on the size and shape of the device 1310 and other components with which the insertion tool 1370 is used. The insertion tool 1370 can generally be configured in a manner that is complementary to the design of the device 1310. For example, in the illustrated embodiment, the distal end 1370*d* of the insertion tool 1370 is generally flat and has a diameter similar to the diameter of the anchor 1312, and the diameter of the insertion tool bore 1376 is similar to the diameter of the anchor bore 1316 so that the two bores 1376, 1316 can be substantially aligned in use. Of course, there is no requirement that these configurations be complementary provided the two components can be adequately coupled for purposes of inserting the device 1310 into bone. In some embodiments the insertion tool 1370 can have a diameter in the range of about 1 millimeter to about 12 millimeters, and in one embodiment it has a diameter of about 2 millimeters, and in some embodiments it can have a length in the range of about 5 centimeters to about 40 centimeters, and in one embodiment it has a length of about 25 centimeters. Any number of materials known to those skilled in the art for forming insertion tools and handles can be used to form the insertion tool 1370 and handle 1372, including but not limited to polymers and metals. In one exemplary embodiment the insertion tool 1370 is formed from stainless steel and its handle 1372 is formed from polycarbonate.

As shown in FIG. 18, an insertion assembly 1300 can include the device 1310, the insertion tool 1370, a guide portion 1380, and a spacer element 1390, and can be used to place the device 1310 in bone. The guide portion 1380 can be an elongate tube that is disposed around at least a portion of the insertion tool 1370 and a portion of the anchor 1312. As a result, as shown in FIG. 18, a distal portion 1380*d* of the guide portion 1380 can hold the connecting filament 1317 against the anchor 1312 in embodiments of the device 1312 in which the connecting filament 1317 would otherwise fall distally due to gravity. The guide portion 1380 can also be used to align the device 1310 and the insertion tool 1370 with the bore of the bone in which the device 1310 is to be disposed, as described in further detail below with respect to FIGS. 19A-19E. A proximal end 1380*p* of the guide portion 1380 can include a handle 1382 that can be used by a surgeon to grip the guide portion 1380 and can also provide additional support for the spacer 1390 to sit on as shown.

The spacer element 1390 can be any removable component configured to maintain a space between the handle 1372 of the insertion tool 1370 and the handle 1382 of the guide portion 1380 when the spacer element 1390 is disposed between the insertion tool 1370 and the guide portion 1380. The spacer element 1390 can prevent the insertion tool 1370 from being moved distally. Such distal movement by the insertion tool would cause the anchor 1312 to move distally into the bore 1002. Consequently, removal of the spacer element 1390 can allow the insertion tool handle 1372 to be moved toward the guide portion handle 1382 to insert the anchor 1312 into the bore, as described in greater detail below with respect to FIGS. 19A-19E. In the illustrated embodiment the spacer 1390 is a tubular block adapted to sit primarily on one side of the insertion tool 1370, although in other embodiments the spacer can sit primarily on the other side of the insertion tool 1370 or substantially on both sides of the insertion tool 1370. A person skilled in the art would recognize a number of other components and configurations that can be used in place of the spacer element 1390 to allow for selective movement of the insertion tool 1370 toward the guide portion 1380 to move the device 1310 distally into the bore 1002.

The guide portion 1380 and spacer element 1390 can have a variety of shapes and configurations, depending at least in part on the shapes and dimensions of the insertion tool 1370, the device 1310, and the components thereof. By way of non-limiting example, a diameter of the guide portion 1380 can typically be just larger than a diameter of the insertion tool 1370 so that a connecting filament 1317 disposed therebetween can be held in place. In some embodiments the guide portion 1380 can have a diameter in the range of about 1 millimeters to about 13 millimeters, and in one embodiment it has a diameter of about 2.5 millimeters, and can have a length in the range of about 7 centimeters to about 50 centimeters, and in one embodiment it has a length of about 30 centimeters. A length of the spacer element 1390 can be configured based on the desired insertion depth of the anchor 1312 into the bore 1002 because once the spacer element 1390 is removed, the insertion tool 1370 can slide distally until the insertion tool handle 1372 abuts the guide portion handle 1382. The distance traveled by the insertion tool 1370 can also be the distance traveled by the anchor 1312 coupled thereto. Thus, if it is desired that a proximal end 1312*p* of the anchor 1312 is substantially flush with a surface of the bone, a length of the spacer element 1390 can be approximately equal to a length of the anchor 1312 less any length of the anchor 1312 that extends distally beyond the guide portion 1380 when the guide portion 1380 is disposed around the anchor 1312. In some embodiments the spacer element 1390 can have a length in the range of about 3 millimeters to about 25 millimeters, and in one embodiment it has a length of about 10 millimeters. A person skilled in the art would recognize other configurations that can be used with respect to the device 1310, insertion tool 1370, and guide portion 1380 to achieve desired insertion depths without departing from the spirit of the present disclosures. Further, any number of materials known to those skilled in the art for forming guide portions and spacer elements can be used to form the guide portion 1380, its handle 1382, and the spacer element 1390, including but not limited to polymers and metals. In one exemplary embodiment both the guide portion 1380 and the spacer element 1390 are formed from stainless steel, while the guide portion handle 1382 is formed from polycarbonate.

FIGS. 19A-19E illustrate one exemplary method for performing a tissue repair using the insertion assembly 1300 to insert the device 1310 into a bore 1002 formed in bone 1001. A surgical opening can be formed through skin and a cannula can be passed therethrough to access a surgical repair site according to well known techniques. Similar to FIGS. 5A-5G, although cannulas are often used to define a channel through which the procedure can be preformed, the cannula is not shown in FIGS. 19A-19E for clarity of illustration. Accordingly, to the extent the figures show components of the systems and devices passing through skin, these components would typically be extending through the cannula, which itself is passed through the skin.

The bore 1002 can be formed in the bone 1001 in which the device 1310 is to be disposed using techniques known to those having skill in the art. As shown in FIG. 19A, once the insertion assembly 1300 is assembled by coupling the anchor 1312 to the insertion tool 1370, disposing the guide portion 1380 around the insertion tool 1370, and disposing the spacer element between the guide portion 1380 and the insertion tool 1370, the assembly 1300 can be moved to a location that is proximate to the bore 1002 for insertion of the device 1310 therein. As shown in FIG. 19B, the distal end 1380*d* of the guide portion 1380 can abut each side of the bone 1001 adjacent to the bore 1002, while the distal side 1312*d* of the anchor 1312 can be inserted into the bore 1002. The connecting filament 1317 can be disposed between the distal side 1312*d* of the anchor 1312 and the walls of the bore due to the guide portion 1380 maintaining the ends of the connecting filament 1317 between the guide portion 1380 and the anchor 1312.

Figure 19E:
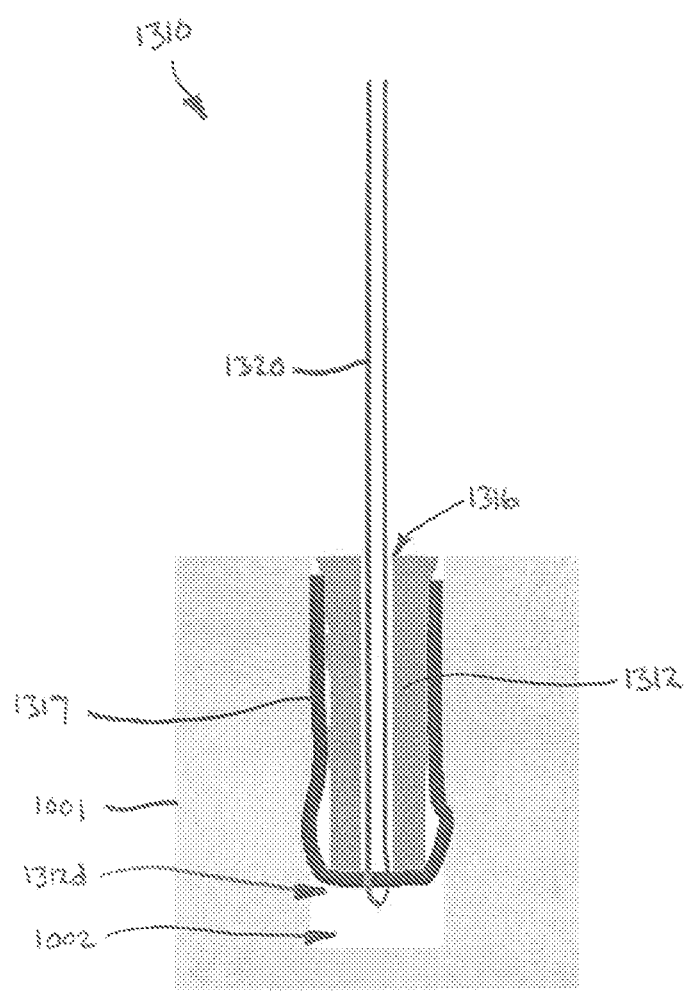

As shown in FIG. 19C, the spacer element 1390 can be removed, and then as shown in FIG. 19D, the insertion tool 1370 can be advanced distally to move the anchor 1312 into the bore 1002. Distal travel of the insertion tool 1370 stops when the insertion tool handle 1372 abuts the guide portion 1382, resulting in the proximal end 1312*p* of the anchor being substantially flush with the bone 1001. In the illustrated embodiment the distance traveled by the anchor 1312 is the approximate length of the spacer element 1390. Because the guide portion 1380 abuts the bore 1002 as the insertion tool 1370 travels distally, as the anchor 1312 slides further out of the guide portion 1380 and into the bore 1002, the connecting filament 1317 can remain disposed adjacent to the anchor 1312, between the anchor 1312 and the walls of the bore 1002. As shown in FIG. 19E, the guide portion 1380 and insertion tool 1370 can be removed, leaving the device 1310 disposed in the bone 1001 with a location of the repair filament 1320 with respect to the anchor 1312 being substantially maintained by the connecting filament 1317 trapped between the anchor 1312 and the walls of the bore 1002. The repair filament 320 can subsequently be used to repair soft tissue as described above, or using other procedures known to those skilled in the art and/or described in other patent applications incorporated by reference herein.

The procedures discussed herein are just some examples of procedures that can be performed in conjunction with systems, devices, and methods disclosed herein. A person skilled in the art will recognize a number of other ways that the disclosed systems, devices, and methods can be used in various other configurations and types of surgical procedures.

One skilled in the art will appreciate further features and advantages of the invention based on the above-described embodiments. Accordingly, the invention is not to be limited by what has been particularly shown and described, except as indicated by the appended claims. Further, although the systems, devices, and methods provided for herein are generally directed to surgical techniques, at least some of the systems, devices, and methods can be used in applications outside of the surgical field. All publications and references cited herein are expressly incorporated herein by reference in their entirety.

What is claimed is:

1. A surgical soft tissue repair device, comprising:
an anchor having a proximal end and a distal end with an axial bore extending therethrough from the proximal end to the distal end, the anchor having a plurality of bone-engaging features disposed on an outer surface thereof, and the anchor being configured to be fixated in bone;
a repair filament;
a connecting filament disposed through the axial bore, the connecting filament being configured to couple to the repair filament, with the repair filament being configured to bring the connecting filament from an unstressed configuration in which the connecting filament is not fixedly coupled to the anchor into an anchoring configuration in which the connecting filament engages the anchor within a distal portion of the axial bore and positions the repair filament with respect to the anchor,
wherein a distal end of the connecting filament has a diameter that is greater than a diameter of the axial bore when the connecting filament is in the anchoring configuration.

2. The device of claim 1, wherein the repair filament is in sliding engagement with the connecting filament.

3. The device of claim 1, wherein the connecting filament comprises a loop disposed in the axial bore, the loop extending from a proximal end of the connecting filament to the distal end of the connecting filament when the connecting filament is in the anchoring configuration, the distal end of the connecting filament closing the loop within the distal portion of the axial bore.

4. The device of claim 3, wherein the connecting filament extends proximal of the proximal end of the anchor.

5. The device of claim 3,
wherein a width of the connecting filament in the unstressed configuration is less than the diameter of the axial bore such that the connecting filament in the unstressed configuration is capable of being moved from the proximal end to the distal end of the anchor by passing the connecting filament distally through the axial bore.

6. The device of claim 5, wherein the distal end of the connecting filament is configured to be actuated to transition the connecting filament from the unstressed configuration to the anchoring configuration.

7. The device of claim 1, wherein the connecting filament does not pass through the axial bore when tension is applied to the repair filament in a proximal direction when the connecting filament is in the anchoring configuration.

8. The device of claim 1, wherein the repair filament comprises a snare assembly having a collapsible snare at one end thereof, a terminal end opposite the collapsible snare, and an intermediate portion therebetween, the anchor being positioned along the intermediate portion.

9. The device of claim 1, wherein the axial bore comprises a stepped portion such that the distal portion of the axial bore has a diameter that is larger than a proximal portion of the axial bore.

10. The device of claim 1, wherein the connecting filament is disposed through the axial bore from the distal portion of the axial bore to a location that is at least one of proximate to the proximal end of the anchor, at the proximal end of the anchor, or proximal of the proximal end of the anchor.

11. A surgical method, comprising:
  implanting an anchor in a bore formed in a bone, the anchor having a proximal end and a distal end with an axial bore extending between a proximal-most end of the proximal end to a distal-most end of the distal end such that an inner diameter of the axial bore is stepped to have a first, smaller diameter at the proximal-most end that extends towards a second, greater diameter at the distal-most end, the anchor having a plurality of bone-engaging features disposed on an outer surface thereof, and the anchor having a connecting filament disposed through the axial bore such that a distal end of the connecting filament is disposed within a distal portion of the axial bore and a proximal end of the connecting filament is disposed at least one of proximate to the proximal end of the anchor, at the proximal end of the anchor, or proximal of the proximal end of the anchor;
  passing a terminal end of a repair filament coupled to the connecting filament into and through at least a portion of tissue detached from the bone; and
  operating the repair filament to draw the tissue towards the bone.

12. The method of claim 11, wherein the repair filament comprises a snare assembly having a collapsible snare at one end thereof and at least one elongate filament extending therefrom, the at least one elongate filament having a terminal end opposite the collapsible snare, and operating the repair filament to draw the tissue towards the bone further comprises:
  inserting the terminal end of the at least one elongate filament through the collapsible snare;
  collapsing the collapsible snare around the at least one elongate filament; and
  sliding the collapsed snare toward the tissue to apply tension to the at least one filament between the anchor and the tissue so as to bring the tissue into proximity with the bone.

13. The method of claim 11, wherein coupling the repair filament to the connecting filament occurs prior to implanting the anchor in the bore formed in the bone.

14. The method of claim 11, wherein coupling the repair filament to the connecting filament occurs after implanting the anchor in the bore formed in the bone.

15. The method of claim 14, further comprising coupling the repair filament to the connecting filament.

16. The method of claim 15, wherein coupling the repair filament to the connecting filament further comprises passing the repair filament through a loop formed by the connecting filament to cause a sliding engagement between the repair filament and the connecting filament proximate to the proximal end of the anchor, the loop being disposed in the axial bore.

17. The method of claim 16, wherein the sliding engagement occurs proximal of the proximal end of the anchor.

18. The method of claim 17, wherein the connecting filament is disposed in an anchoring configuration in which the connecting filament engages the anchor within the distal portion of the axial bore to set a location of the connecting filament with respect to the anchor and the distal end of the connecting filament is unable to pass proximally through the axial bore.

19. The method of claim 18, further comprising:
  after implanting the anchor in the bore formed in the bone, actuating the connecting filament to cause the connecting filament to transition from an unstressed configuration in which the connecting filament is capable of being passed fully through the axial bore to the anchoring configuration in which a width of the connecting filament increases to a size that prevents the connecting filament from passing through the axial bore.

20. The method of claim 11, wherein the connecting filament is disposed in an anchoring configuration in which the connecting filament engages the anchor within the distal portion of the axial bore to set a location of the connecting filament with respect to the anchor and the distal end of the connecting filament is unable to pass proximally through the axial bore.

21. The method of claim 20, further comprising:
  actuating the connecting filament to cause the connecting filament to transition from an unstressed configuration in which the connecting filament is capable of being passed fully through the axial bore to the anchoring configuration in which a width of the connecting filament increases to a size that prevents the connecting filament from passing through the axial bore.

22. The method of claim 11, further comprising:
  passing the connecting filament through the axial bore such that the distal end of the connecting filament is disposed within the distal portion of the axial bore and the proximal end of the connecting filament is disposed at least one of proximate to the proximal end of the anchor, at the proximal end of the anchor, or proximal of the proximal end of the anchor.

23. The method of claim 11, wherein the inner diameter is substantially uniform from the proximal end to a location adjacent to the distal portion in which the connecting filament is disposed.

24. The method of claim 11, wherein the inner diameter does not decrease from the proximal-most end to the distal-most end.

25. A surgical method, comprising:
  implanting an anchor in a bore formed in a bone, the anchor having a proximal end and a distal end with an axial bore extending therethrough from the proximal end to the distal end, the anchor having a plurality of bone-engaging features disposed on an outer surface thereof, and the anchor having a connecting filament disposed through the axial bore such that a distal end of the connecting filament is disposed within a distal portion of the axial bore and a proximal end of the connecting filament is disposed at least one of proximate to the proximal end of the anchor, at the proximal end of the anchor, or proximal of the proximal end of the anchor;
  coupling a repair filament to the connecting filament;
  passing a terminal end of the repair filament coupled to the connecting filament into and through at least a portion of tissue detached from the bone; and
  operating the repair filament to draw the tissue towards the bone,
  wherein coupling the repair filament to the connecting filament occurs after implanting the anchor in the bore formed in the bone.

26. The method of claim 25, wherein coupling the repair filament to the connecting filament further comprises passing the repair filament through a loop formed by the connecting filament to cause a sliding engagement between the repair filament and the connecting filament proximate to the proximal end of the anchor, the loop being disposed in the axial bore.

27. The method of claim 26, wherein the sliding engagement occurs proximal of the proximal end of the anchor.

28. The method of claim 27, wherein the connecting filament is disposed in an anchoring configuration in which the connecting filament engages the anchor within the distal portion of the axial bore to set a location of the connecting filament with respect to the anchor and the distal end of the connecting filament is unable to pass proximally through the axial bore.

29. The method of claim 28, further comprising:
   after implanting the anchor in the bore formed in the bone, actuating the connecting filament to cause the connecting filament to transition from an unstressed configuration in which the connecting filament is capable of being passed fully through the axial bore to the anchoring configuration in which a width of the connecting filament increases to a size that prevents the connecting filament from passing through the axial bore.

* * * * *